(12) United States Patent
Li et al.

(10) Patent No.: US 8,367,839 B2
(45) Date of Patent: Feb. 5, 2013

(54) TETRAKIS(1-IMIDAZOLYL) BORATE (BIM4) BASED ZWITTERIONIC AND RELATED MOLECULES USED AS ELECTRON INJECTION LAYERS

(75) Inventors: Huaping Li, Goleta, CA (US); Yunhua Xu, Hyattsville, MD (US); Guillermo C. Bazan, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/592,761

(22) Filed: Dec. 1, 2009

(65) Prior Publication Data

US 2010/0145062 A1    Jun. 10, 2010

Related U.S. Application Data

(60) Provisional application No. 61/118,906, filed on Dec. 1, 2008.

(51) Int. Cl.
*C07D 403/14* (2006.01)
*C07F 5/02* (2006.01)

(52) U.S. Cl. ........................................ 548/110
(58) Field of Classification Search ........... 548/110
See application file for complete search history.

(56) References Cited

U.S. PATENT DOCUMENTS

2006/0124902 A1   6/2006 Ziegler

OTHER PUBLICATIONS

Li et al. J. Am. Chem. Soc, 2009, 131, 8903-8912.*
Tang, C. W.; Vanslyke, S. A. Appl. Phys. Lett. 1987, 51, 913-915.
Burroughes, J. H.; Bradley, D. D. C.; Brown, A. R.; Marks, R. N.; Mackay, K.; Friend, R. H.; Burns, P. L.; Holmes, A. B. Nature 1990, 347, 539-541.
Kraft, A.; Grimsdale, A. C.; Holmes, A. B. Angew. Chem., Int. Ed. 1998, 37, 402-428.
Sirringhaus, H.; Tessler, N.; Friend, R. H. Science 1998, 280, 1741-1744.
Dimitrakopoulos, C. D.; Malenfant, P. R. L. AdV. Mater. 2002, 14, 99-117.
Walzer, K.; Maennig, B.; Pfeiffer, M.; Leo, K. Chem. ReV. 2007, 107, 1233-1271.
Tang, C. W. Appl. Phys. Lett. 1986, 48, 183-185.
Brabec, C. J.; Sariciftci, N. S.; Hummelen, J. C. AdV. Funct. Mater. 2001, 11, 15-26.
Kim, J. Y.; Lee, K.; Coates, N. E.; Moses, D.; Nguyen, T.-Q.; Dante, M.; Heeger, A. .Science 2007, 317, 222-225.
Aroca, R.; Del Cano, T.; de Saja, J. A. Chem. Mater. 2003, 15, 38-45.
Snaith, H. J.; Whiting, G. L.; Sun, B. Q.; Greenham, N. C.; Huck, W. T. S.; Friend, R. H. Nano Lett. 2005, 9, 1653-1657.
Kim, Y.; Cook, S.; Tuladhar, S. M.; Nelson, J.; Durrant, J. R.; Bradley, D. D. C.; Giles, M.; McCulloch, I.; Ha, C. S.; Ree, M. Nat. Mater. 2006, 5, 197-203.
Yamamoto, Y.; Fukushima, T.; Saeki, A.; Seki, S.; Tagawa, S.; Ishii,N.; Aida, T. J. Am. Chem. Soc. 2007, 129, 9276-9277.
Johkheijm, P.; Stutzmann, N.; Chen, Z. J.; de Leeuw, D. M.; Meijer, E. W.; Schenning, A. P. H. J.; Wurthner, F. J. Am. Chem. Soc. 2006, 128, 9535-9540.
Garnier, F.; Yassar, A.; Hajlaoui, R.; Horowitz, G.; Deloffre, F.; Servet,B.; Ries, S.; Alnot, P. J. Am. Chem. Soc. 1993, 115, 8716-8721.
Kastler, M.; Pisula, W.; Laquai, F.; Kumar, A.; Davies, R. J.;Baluschev, S.; Garcia-Gutierrez, M. C.; Wasserfullen, D.; Butt, H. J.;Riekel, C.; Wegner, G.; Mullen, K. AdV. Mater. 2006, 18, 2255-2259.
Kline, R. J.; McGehee, M. D.; Toney, M. F. Nat. Mater. 2006, 5,222-228.
Duhm, S.; Heimel, G.; Salzmann, I.; Glowatzkl, H.; Johnson, R. L.;Vollmer, A.; Rabe, J. P.; Koch, N. Nat. Mater. 2008, 7, 326-332.
Stoliar, P.; Kshirsagar, R.; Massi, M.; Annibale, P.; Albonetti, C.; deLeeuw, D. M.; Biscarini, F. J. Am. Chem. Soc. 2007, 129, 6477-6484.
Holman, M. W.; Liu, R. C.; Adams, D. M. J. Am. Chem. Soc. 2003,125, 12649-12654.
Liu, M. S.; Niu, Y.-H.; Luo, J.; Chen, B.; Kim, T.-D.; Bardecker, J.;Jen, A. K.-Y. Polym. ReV. 2006, 46, 7-26.
Hung, L. S.; Tang, C. W. Appl. Phys. Lett. 1999, 74, 3209-3211.
Greenham, N. C.; Moratti, S. C.; Bradley, D. D. C.; Friend, R. H.;Holmes, A. B. Nature 1993, 365, 628-630.
Brewer, P. J.; Lane, P. A.; deMello, A. J.; Bradley, D. D. C.; de Mello,J. C. AdV. Funct. Mater. 2004, 14, 562-570.
Parker, I. D. J. Appl. Phys. 1994, 75, 1656-1666.
Malliaras, G. G.; Scott, J. C. J. Appl. Phys. 1998, 83, 5399-5403.
Ho, P. K. H.; Kim, J.-S.; Burroughes, J. H.; Becker, H.; Li, S. F. Y.;Brown, T. M.; Cacialli, F.; Friend, R. H. Nature 2000, 404, 481-484.
Yang, X.; Müller, D. C.; Neher, D.; Meerholz, K. AdV. Mater. 2006,18, 948-954.
Hung, L. S.; Tang, C. W.; Mason, M. G. Appl. Phys. Lett. 1997, 70,152-154.
Li, F.; Tang, H.; Anderegg, J.; Shinar, J. Appl. Phys. Lett. 1997, 70,1233-1235.
Huang, J.; Li, G.; Wu, E.; Xu, Q.; Yang, Y. AdV. Mater. 2006, 18,114-117.
Ishii, H.; Sugiyama, K.; Ito, E.; Seki, K. AdV. Mater. 1999, 11, 605-625.
Heimel, G.; Romaner, L.; Zojer, E.; Bredas, J.-L. Acc. Chem. Res. 2008, 4, 721-729.
Shen, Y. L.; Hosseini, A. R.; Wong, M. H.; Malliaras, G. G. Chem. Phys. Chem. 2004, 5, 16-25.
Campbell, I. H.; Joswick, M. D.; Parker, I. D. Appl. Phys. Lett. 1995,67, 3171-3173.

(Continued)

*Primary Examiner* — Joseph Kosack
*Assistant Examiner* — Matthew Coughlin
(74) *Attorney, Agent, or Firm* — Berliner & Associates

(57) ABSTRACT

Tetrakis(1-imidazolyl)borate (BIm4) based zwitterionic and/or related molecules for the fabrication of PLEDs is provided. Device performances with these materials approaches that of devices with Ba/Al cathodes for which the cathode contact is ohmic. Methods of producing such materials, and electron injection layers and devices containing these materials are also provided.

4 Claims, 13 Drawing Sheets

OTHER PUBLICATIONS

Hoven, C. V.; Peet, J.; Mikhailovsky, A.; Nguyen, T.-Q. Appl. Phys. Lett. 2009, 94, 033301. 1-3.

Huang, F.; Wu, H. B.; Wang, D.; Yang, W.; Cao, Y. Chem. Mater. 2004, 16, 708-716.

Hoven, C. V.; Garcia, A.; Bazan, G. C.; Nguyen, T. Q. AdV. Mater. 2008, 20, 3793-3810.

Yang, R. Q.; Wu, H. B.; Cao, Y.; Bazan, G. C. J. Am. Chem. Soc. 2006, 128, 14422-14423.

Steuerman, D. W.; Garcia, A.; Dante, M.; Yang, R.; Lofvander, J. P.; Nguyen, T. Q. AdV. Mater. 2008, 20, 528-534.

Hoven, C.; Yang, R.; Garcia, A.; Heeger, A. J.; Nguyen, T. Q.; Bazan, G. C. J. Am. Chem. Soc. 2007, 129, 10976-10977.

Hoven, C. V.; Yang, R.; Garcia, A.; Crockett, V.; Heeger, A. J.; Bazan, G. C.; Nguyen, T. Q. Proc. Natl. Acad. Sci. U.S.A. 2008, 105, 12730-12735.

Yang, R. Q.; Xu, Y. H.; Deng, X. D.; Nguyen, T. Q.; Cao, Y.; Bazan, G. C. J. Am. Chem. Soc. 2008, 130, 3282-3283.

Xu, Y. H.; Yang, R. Q.; Peng, J. B.; Mikhailovsky, A. A.; Cao, Y.; Nguyen, T.-Q.; Bazan, G. C. AdV. Mater. 2009, 21, 584-588.

Hamilton, B. H.; Kelly, K. A.; Malasi, W.; Ziegler, C. J. Inorg. Chem. 2003, 42, 3067-3073.

Kirchmeyer, S.; Reuter, K. J. Mater. Chem. 2005, 15, 2077-2088.

Tang, H.; Li, F.; Shinar, J. Appl. Phys. Lett. 1997, 71, 2560-2562.

Hsiao, C.-C.; Hsiao, A.-E.; Chen, S.-A. AdV. Mater. 2008, 20, 1982-1988.

Tang, C. W.; Vanslyke, S. A.; Chen, C. H. J. Appl. Phys. 1989, 65, 3610-3616.

Cao, Y.; Yu, G.; Heeger, A. J. AdV. Mater. 1999, 10, 917-920.

Huang, F.; Hou, L. T.; Wu, H. B.; Wang, X. H.; Shen, H. L.; Cao, W.; Yang, W.; Cao, Y. J. Am. Chem. Soc. 2004, 126, 9845-9853.

Wu, H.; Huang, F.; Mo, Y.; Yang, W.; Wang, D.; Peng, J.; Cao, Y. AdV. Mater. 2004, 16, 1826-1830.

Pei, Q. B.; Zhang, C.; Yang, Y.; Heeger, A. J. Science 1995, 269, 1086-1088.

Pei, Q. B.; Yang, Y.; Yu, G.; Zhang, C.; Heeger, A. J. J. Ann. Chem. Soc. 1996, 118, 3922-3929.

Slinker, J. D.; DeFranco, J. A.; Jaqith, M. J.; Silveira, R.; Zhong, Y.-W.; Moran-Mirabal, J. M.; Craighead, H. G.; Abru-na, H. D.; Marohn, J. A.; Malliaras, G. G. Nat. Mater. 2007, 6, 894-899.

Pingree, L. S. C.; Rodovsky, D. B.; Coffey, D. C.; Bartholomew, G. P.; Ginger, D. S. J. Am. Chem. Soc. 2007, 129, 15903-15910.

Coffey, D. C.; Ginger, D. S. Nat. Mater. 2006, 5, 735-740.

Hoppe, H.; Glatzel, T.; Niggemann, M.; Hinsch, A.; Lux-Steiner, M. C.; Sariciftci, N. S. Nano Lett. 2005, 5, 269-274.

Chiesa, M.; Burgi, L.; Kim, J. S.; Shikler, R.; Friend, R. H.; Sirringhaus, H. Nano Lett. 2005, 5, 559-563.

Liscio, A.; De Luca, G.; Nolde, F.; Palermo, V.; Mullen, K.; Samori, P. J. Am. Chem. Soc. 2008, 130, 780-781.

Girard, P. Nanotechnology 2001, 12, 485-490.

* cited by examiner

TETRAKIS(1-IMIDAZOLYL) BORATE (BIM4) BASED ZWITTERIONIC AND RELATED MOLECULES USED AS ELECTRON INJECTION LAYERS

CROSS-REFERENCE TO RELATED APPLICATIONS

This application claims the benefit of U.S. Provisional Patent Application No. 61/118,906 filed Dec. 1, 2008, which is hereby incorporated by reference in its entirety.

STATEMENT REGARDING FEDERALLY SPONSORED RESEARCH OR DEVELOPMENT

This invention was made with Government support under Grant No. SSL-DOE 8-448 777 22 412 from the Department of Energy. The Government has certain rights in this invention.

FIELD OF THE INVENTION

This invention relates generally to the field of electron injecting/transport layers in polymer light emitting diodes. More particularly, it concerns the methods and devices incorporating zwitterionic and/or related molecules based on a borate core in these layers.

BACKGROUND OF THE INVENTION

Organic semiconducting molecules and polymers are promising components in emerging optoelectronic technologies, such as light emitting devices,[1-3] flexible thin film transistors,[4-6] and plastic solar cells.[7-9] An important potential advantage, relative to inorganic systems, is the possibility to deposit device layers directly from solution and thereby to simplify fabrication methods. Physical organic chemistry principles can be used to tailor molecular properties relevant for function including emission color, ionization potential and electron affinity. However, the bulk behavior is more difficult to predict as the final organization in the solid is mediated by weak intermolecular forces and is therefore dependent on the deposition history and subsequent fabrication steps. Intermolecular order can control, for example, emission output,[10] charge generation efficiencies in photovoltaic devices[11-14] and the mobilities of charge carriers.[15-17] The problem of predicting function from molecular design is exacerbated at metal/organic interfaces, where the molecular orientation of even a monolayer can have a substantial effect on the electric field required for charge injection.[18-21]

Electron injection from a metal electrode is an important longstanding area of interest within the scope of organic light emitting diodes (LEDs).[22-24] In the absence of interfacial effects, the electron current is limited to a combination of Fowler-Nordheim tunneling and thermionic emission mechanisms where the barrier corresponds to the difference in energy levels between the cathode work function and the π*-band (lowest unoccupied molecular orbital) of the semiconducting polymer.[25] Injection barriers, which are large for stable metals such as Al due to their high work function, increase the operational voltage and can lead to unbalanced hole and electron currents and low electroluminescence efficiencies.[26-28] They are therefore an essential problem in the design of organic optoelectronic materials. Based on the considerations above, electron transporting/injection layers (ETLs) have been incorporated within organic LEDs.[29-31] These layers reduce the electron injection barrier by a variety of mechanisms, including placing a dipole adjacent to the cathode,[32,33] band bending using doped materials to create ohmic contacts[34] or through a redistribution of energy levels via charge accumulation.[35,36] Conjugated polyelectrolytes, i.e. conjugated polymers bearing pendant groups with ionic functionalities, have recently been used as effective ETLs.[37-39] That these polymers are soluble in polar solvents offers a practical advantage to eliminate dissolution of non-polar underlying layers.[40] The presence of the ionic component can lead to long response times when ion motion and the resulting electric field redistribution play a fundamental role in improving injection.[41,42] Conjugated oligoelectrolytes have been similarly used as ETLs to improve electron injection.[43,44] The charge compensating counterions in both types of materials are an important ingredient in determining the final performance of the device. A recent study showed that tetrakis(1-imidazolyl)borate (BIm4) proved to be a particularly useful anion when coupled with either cationic conjugated polyelectrolytes or oligoelectrolytes.[39-44]

BRIEF SUMMARY OF THE INVENTION

Provided are methods that provides a new class of zwitterionic and/or related molecules/compounds by the addition of iodoalkane reagents to NaBIm4 molecules. These molecules/compounds can be incorporated via solution methods into polymer LEDs (PLEDs) to display high efficiencies as a result of improved electron injection. Using these methods unexpected structural transformations of the film upon metal evaporation are evident. The end result is a spontaneously formed dipole layer at the organic metal interface that is suitably aligned to modify the effective work function of the cathode.

Notwithstanding the above drawbacks, the present inventors realized that the addition of alkylating reagents such as alkyl halides, and alkyl tosylates to NaBIm4 provides zwitterionic and related molecules that function as excellent ETLs and that can be incorporated via solution methods into PLEDs containing Al cathodes that have luminance (L) efficiencies comparable to those with Ba cathodes.

In one embodiment, a zwitterionic and/or related molecules comprising: a compound of the following formula:

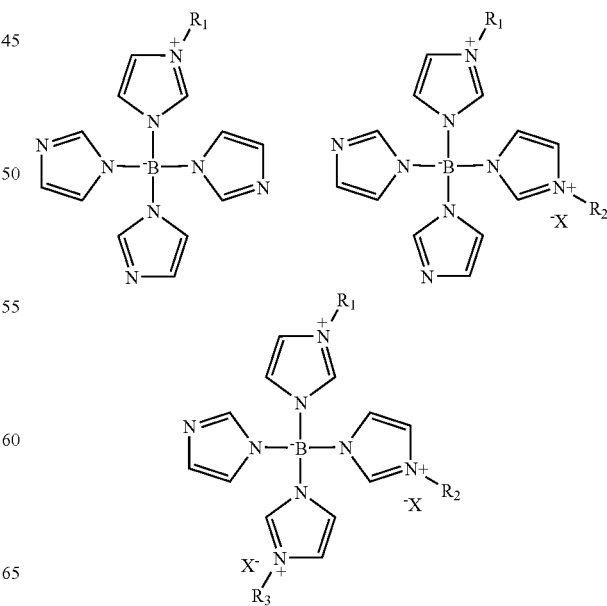

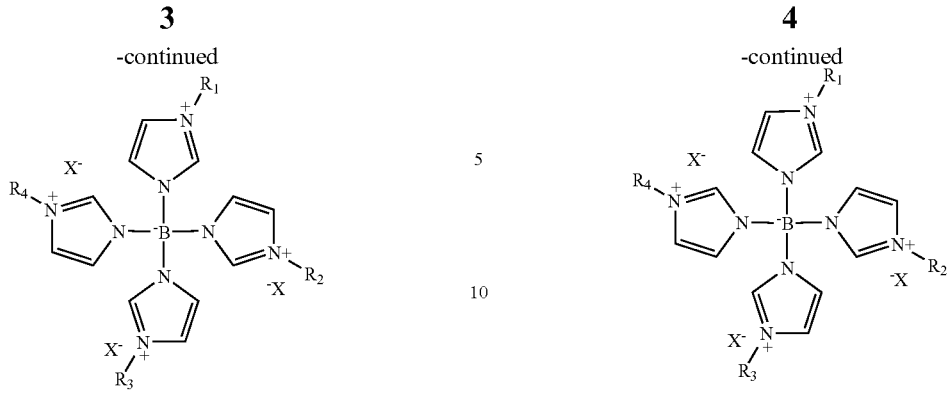

wherein $R_1$, $R_2$, $R_3$ and $R_4$ can each independently be an alkyl, alkene, alkyne, aromatic groups wherein each of the foregoing groups can be with or without heteroatoms and/or charged species; and $X^-$ is a charge compensating anion, such as, but not limited to, halide, borate, nitrate, sulfate, and phosphate.

In a particularized embodiment, $R_1$, $R_2$, $R_3$ and $R_4$ can each independently be a ($C_nH_{2n+1}$) group, where n is an integer from 1-100; more preferably 1-20. In yet a more particularized embodiment, $R_1$, $R_2$, $R_3$ and $R_4$ can each independently be $CH_3$, $C_6H_{13}$, $C_{10}H_{21}$, $C_{12}H_{25}$ or $C_{16}H_{33}$ group, wherein each of the foregoing groups can be with or without heteroatoms and/or charged species.

In another embodiment, a process for producing a zwitterionic and/or related molecules is provided comprising reacting $NaBIm_4$ and R—X, wherein R can be an alkyl, alkene, alkyne, aromatic group wherein each of the foregoing groups can be with or without heteroatoms and/or charged species; and X is a halide, tosyl, borate, nitrate, sulfate, or phosphate.

In yet another embodiment, a light emitting device is provided comprising an electron transport/injecting layer comprising a compound of the following formula:

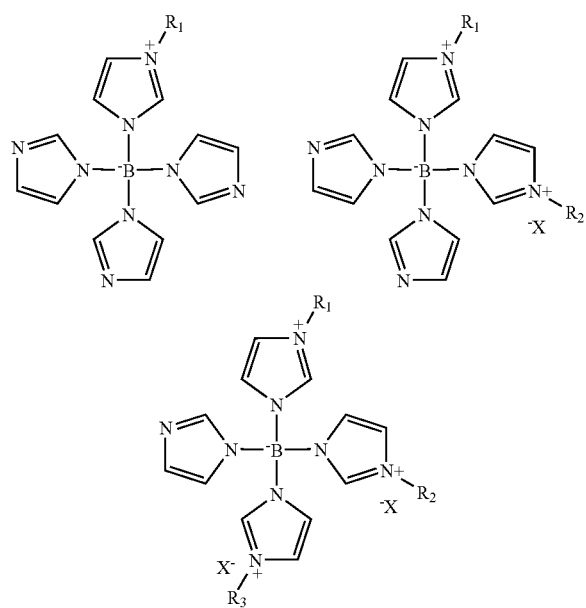

wherein $R_1$, $R_2$, $R_3$ and $R_4$ can each independently be an alkyl, alkene, alkyne, aromatic group, wherein each of the foregoing groups can be with or without heteroatoms and/or charged species; and $X^-$ is a charge compensating anion, such as, but not limited to, halide, borate, nitrate, sulfate, and phosphate.

In a more particularized embodiment, $R_1$, $R_2$, $R_3$ and $R_4$ can each independently comprise a charged species such as, but not limited to quaternary ammonium species such as pyridinium, imidazolium, quinuclidinium; or negative pendant groups ones, including but not limit to sulfonate ($SO_3^-$), phosphate ($PO_4^-$) and carbonate ($CO_2^-$).

In a particularized embodiment, $R_1$, $R_2$, $R_3$ and $R_4$ can each independently be a ($C_nH_{2n+1}$) group, where n is an integer from 1-100. In yet a more particularized embodiment, $R_1$, $R_2$, $R_3$ and $R_4$ can independently be $CH_3$, $C_6H_{13}$, $C_{10}H_{21}$, $C_{12}H_{25}$ or $C_{16}H_{33}$ groups; wherein each of the foregoing groups can be with or without heteroatoms and/or charged species.

In a more particularized embodiment, the above light emitting device has an aluminum cathode.

The advantages of the aforementioned devices are that they have luminance (L) efficiencies comparable to those devices with Ba/Al cathodes.

The performances of the aforementioned devices incorporating charged species as electron injection/transport layers are improved up to 3× of those devices with Ba/Al cathodes.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

TABLE 1

Figure 1:
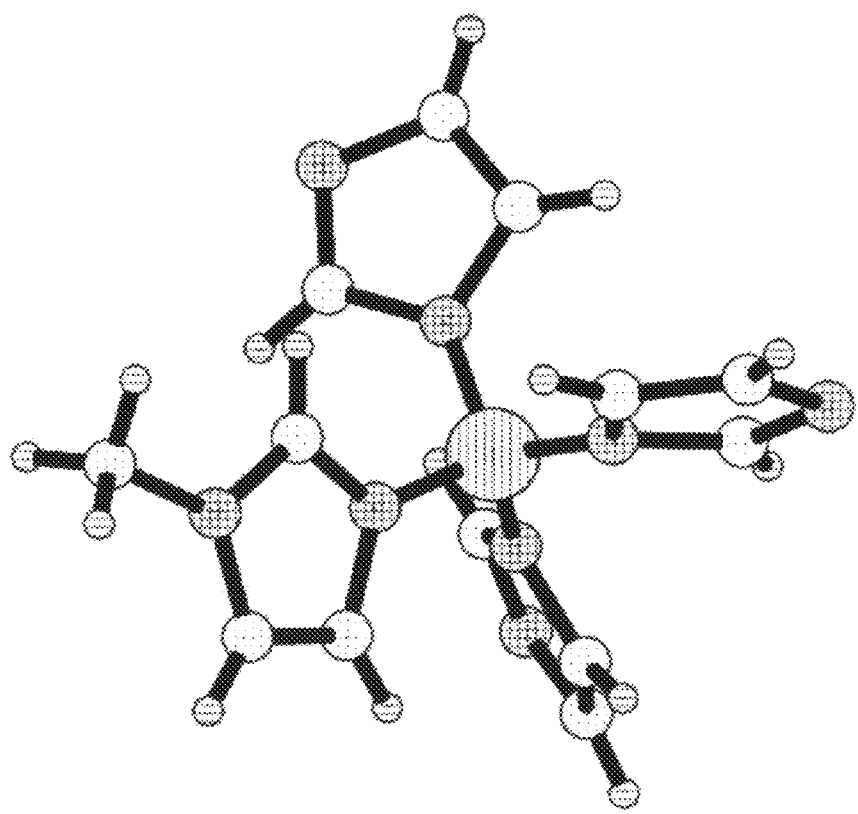
FIG. 1 shows the molecular structure of $C_1$—$BIm_4$ as determined by single crystal X-ray diffraction studies (vertical: B, grid: N, dot: C, horizontal: H).

| Cathode | EML | $V_{turn-on}$ (V) | Maximum Efficiency | | | |
|---|---|---|---|---|---|---|
| | | | cd/A | cd/m² | V | mA/cm² |
| Ba/Al | MEH-PPV | 2 | 1.37 | 2670 | 3.6 | 195 |
| Al | MEH-PPV | 2.6 | 0.01 | 68 | 6 | 828 |
| $C_1$-$BIm_4$/Al | MEH-PPV | 2.6 | 0.01 | 18 | 4 | 323 |
| $C_6$-$BIm_4$/Al | MEH-PPV | 2.3 | 0.24 | 468 | 4.8 | 198 |
| $C_{10}$-$BIm_4$/Al | MEH-PPV | 2.4 | 0.24 | 1547 | 5.4 | 641 |
| $C_{12}$-$BIm_4$/Al | MEH-PPV | 2.2 | 0.60 | 8499 | 6.4 | 1460 |
| $C_{16}$-$BIm_4$/Al | MEH-PPV | 2 | 1.38 | 2156 | 4.2 | 156 |
| $[2C_{16}BIm_4]^+ \cdot I^-$/Al | MEH-PPV | 2.4 | 0.69 | 1402 | 4.6 | 203 |
| $[4C_{16}BIm_4]^+ \cdot 3I^-$/Al | MEH-PPV | 2.4 | 0.02 | 217 | 5.4 | 1092 |
| Ba/Al | PFO | 4.2 | 1.2 | 3904 | 7.2 | 326 |
| Al | PFO | 7.6 | 0.3 | 70 | 8.5 | 30 |
| $[2C_{16}$-$BIm_4]^+ \cdot I^-$/Al | PFO | 5.8 | 3.2 | 8 | 6 | 0.25 |
| $[4C_{10}BIm_4]^+ \cdot 3I^-$/Ba/Al | PFO | 3.2 | 3.1 | 1617 | 4.4 | 51 |
| $[4C_{12}BIm_4]^+ \cdot 3I^-$/Ba/Al | PFO | 3.6 | 2.7 | 352 | 4.4 | 13 |
| $[4C_{16}BIm_4]^+ \cdot 3I^-$/Ba/Al | PFO | 3.3 | 2.9 | 1690 | 4.6 | 58 |

TABLE 2

Device characteristics obtained with different [$C_{16}$-$BIm_4$].

| Cathode | $V_{to}$ (V) | Maximum Efficiency | | | |
|---|---|---|---|---|---|
| | | cd/A | cd/m² | V | mA/cm² |
| 0.0% | 2.6 | 0.01 | 65 | 5.4 | 583 |
| 0.02% | 2.6 | 0.05 | 526 | 7.0 | 1153 |
| 0.05% | 2.0 | 0.56 | 2659 | 4.8 | 474 |
| 0.1% | 2.0 | 1.10 | 1393 | 3.8 | 126 |
| 0.2% | 2.0 | 1.16 | 1201 | 4.4 | 103 |
| 0.3% | 2.4 | 0.94 | 638 | 4.8 | 68 |
| 0.5% | 3.5 | 0.82 | 70 | 4.8 | 8.5 |

Examples of possible alkylating agents that can be used are, but not limited to, alkyl halides, and alkyl tosylates.

Syntheses and Characterization:

Scheme 1 shows the general synthetic entry and structures of the zwitterionic and/or related molecules/compounds. We abbreviate these species by using $C_n$—$BIm_4$, where the subscript "n" corresponds to the number of carbon atoms in the linear alkyl chain attached on nitrogen. The approach involves the addition of alkyl iodides of varying chain lengths to $NaBIm_4$ in dimethylformamide (DMF) at room temperature. An equimolar stoichiometry of reactants yields a mixture of singly and doubly substituted products. The desired monosubstituted product can be obtained in pure form by using chromatography. No doubly or triply charged products due to higher substitution could be detected using the above-mentioned experimental conditions. There was no indication of reaction when alkyl bromides were employed as alkylating agents in ethanol or DMF, 45 even after heating to 80° C. Under appropriate conditions, singly, doubly and triply charged products can be made.

All the complexes in this study were characterized by $^1H$ and $^{13}C$ NMR spectroscopies, mass spectrometry and elemental analysis. As a diagnostic signature for the mono-substituted species, we note that after alkylation the three $^1H$ NMR chemical shifts in $NaBIm_4$ convert to 6 chemical shifts with an integrated ratio of 1:1:1:3:3:3. Alkylation also shifts the signals to lower magnetic fields. Similar trends are observed in the $^{13}C$ NMR chemical shifts. Examination by electrospray ionization mass spectrometry reveals [M+H]$^+$ peaks with an isotopic distribution consistent with the structures in Scheme 1. The abundances of C, H, and N obtained by elemental analysis also match the proposed chemical structures.

Single crystals of $C_1$—$BIm_4$ suitable for X-ray diffraction studies were obtained by slowly evaporating an ethanol solution, and the results are shown in FIG. 1. The geometry of $C_1$—$BIm_4$ is a distorted tetrahedron with substitution taking place at the expected N3 site. The distance of the B—N bond connecting to methylated imidazolyl ring is elongated by approximately 0.09 (2 Å in comparison to the corresponding distances in the unsubstituted rings. The bond lengths of C␎N (neutral Im, 1.354±16 Å; charged Im, 1.332±16 Å) and C═C (neutral Im, 1.350±19 Å; charged Im, 1.342±18 Å) show negligible differences and are similar to those of 1-(3-H-imidazolyl)-tris(1-imidazolyl)borate (H—$BIm_4$).[46] The symmetry of the $C_1$—$BIm_4$ packing unit is $P2_1$/c and includes four molecules packed in parallel along the a axis of the unit cell (see Supporting Information). The distance between two parallel molecules is 6.753±16 Å. Molecular coordinates from the diffraction studies were incorporated into calculations of the molecular dipole moment using the STO-3G basis set in a Gaussian 98 package. These studies gave a dipole on the order of 14±1 D, corresponding to an electron-hole pair separated by ~3 Å, a distance slightly shorter than that of the B—N distance (3.69±2 Å) observed in the solid state.

Incorporation of Zwitterionic and related molecules into PLEDs.

Figure 2:
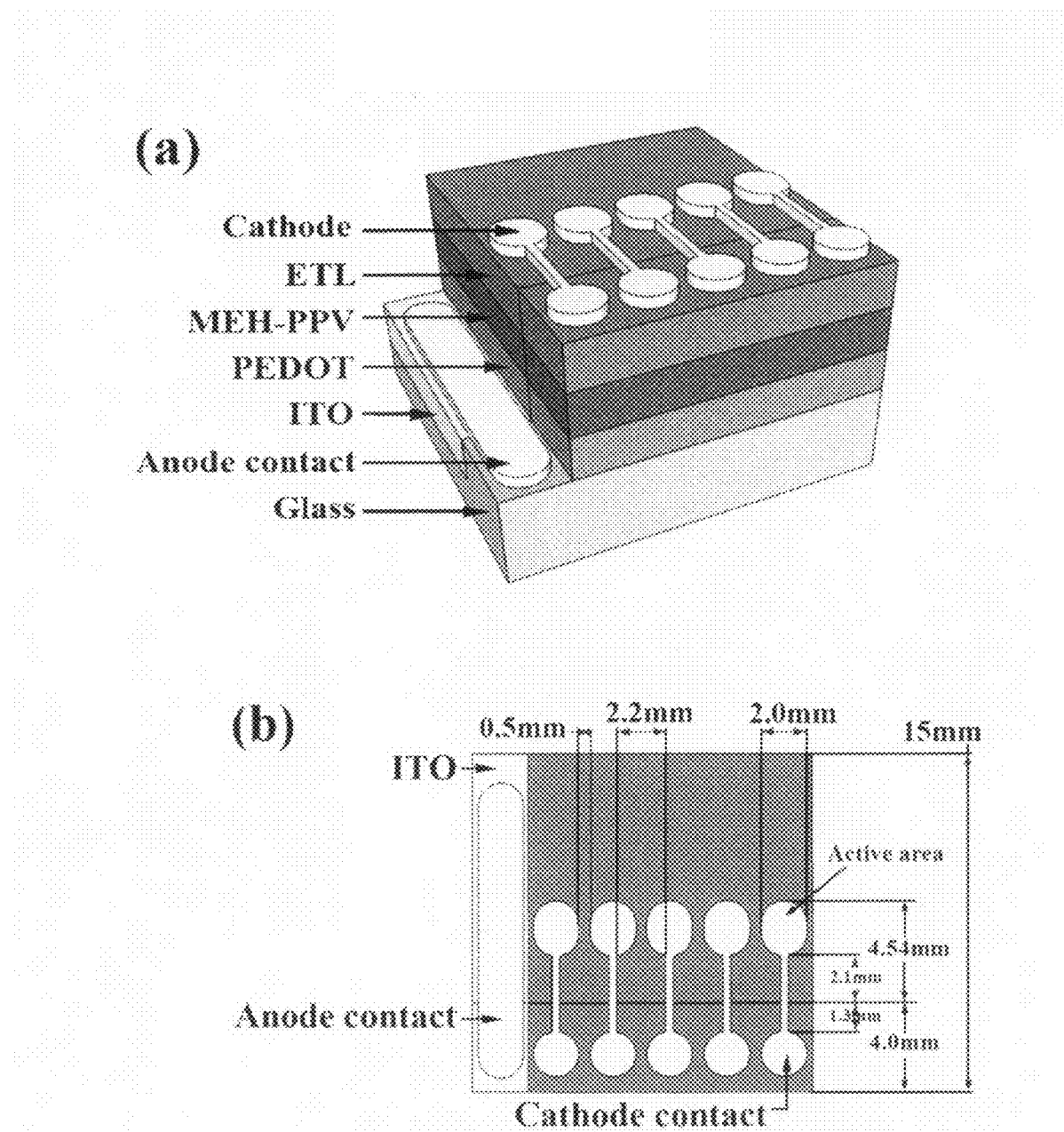
FIG. 2 shows a schematic illustration of the PLED testing platform. Each fabrication provides five independent devices: (a) side view showing the different layers (not to scale) and (b) top view showing the spacing between electrodes.

Whether the zwitterionic and related molecules/compounds in Scheme 1 could be used to modify electron injection into an organic semiconductor was tested within the PLED configuration ITO/PEDOT:PSS/MEHPPV/$C_n$—$BIm_4$/Al, where ITO, PEDOT, PSS and MEH-PPV are indium-tin oxide, poly(3,4-ethylenedioxythiophene), poly (styrenesulfonate) and poly[2-methoxy-5-(2'-ethylhexyloxy-1,4-phenylenevinylene)], respectively. In other PLED configurations, other emissive polymers such as PFO, super yellow were used instead of MEH-PPV. FIG. 2 shows a schematic of the device platform with the internal layers and the cathode patterns/distribution on the surface. The latter information will become relevant when we examine changes of surface characteristics as a function of distance from the electrodes. MEH-PPV or PFO, super yellow was chosen as the conjugated polymer platform due to the fact that it has been widely used in PLED research. It is also possible to use other types of emissive layers known to those of skill in the art. Furthermore, ITO/PEDOT:PSS provides a negligible barrier to hole injection.[47] Electron injection therefore dominates device characteristics and relevant insight on cathode modifications can thereby be obtained. Fabrication begins by spin-coating PEDOT:PSS at 1600 rpm atop cleaned ITO and heating at 180° C. for 10 min. An MEH-PPV layer of approximately 70 nm thickness was then prepared by spin-coating from a toluene solution (0.6%; all concentrations are given in terms of weight fraction in solvent). Layers of $C_n$—$BIm_4$ were deposited from methanol solutions with varying concentrations. Finally, either Al or Ba followed by Al was evaporated at $10^{-6}$ Torr through a mask that gave a 4.8 mm$^2$ contact area.

Figure 3:
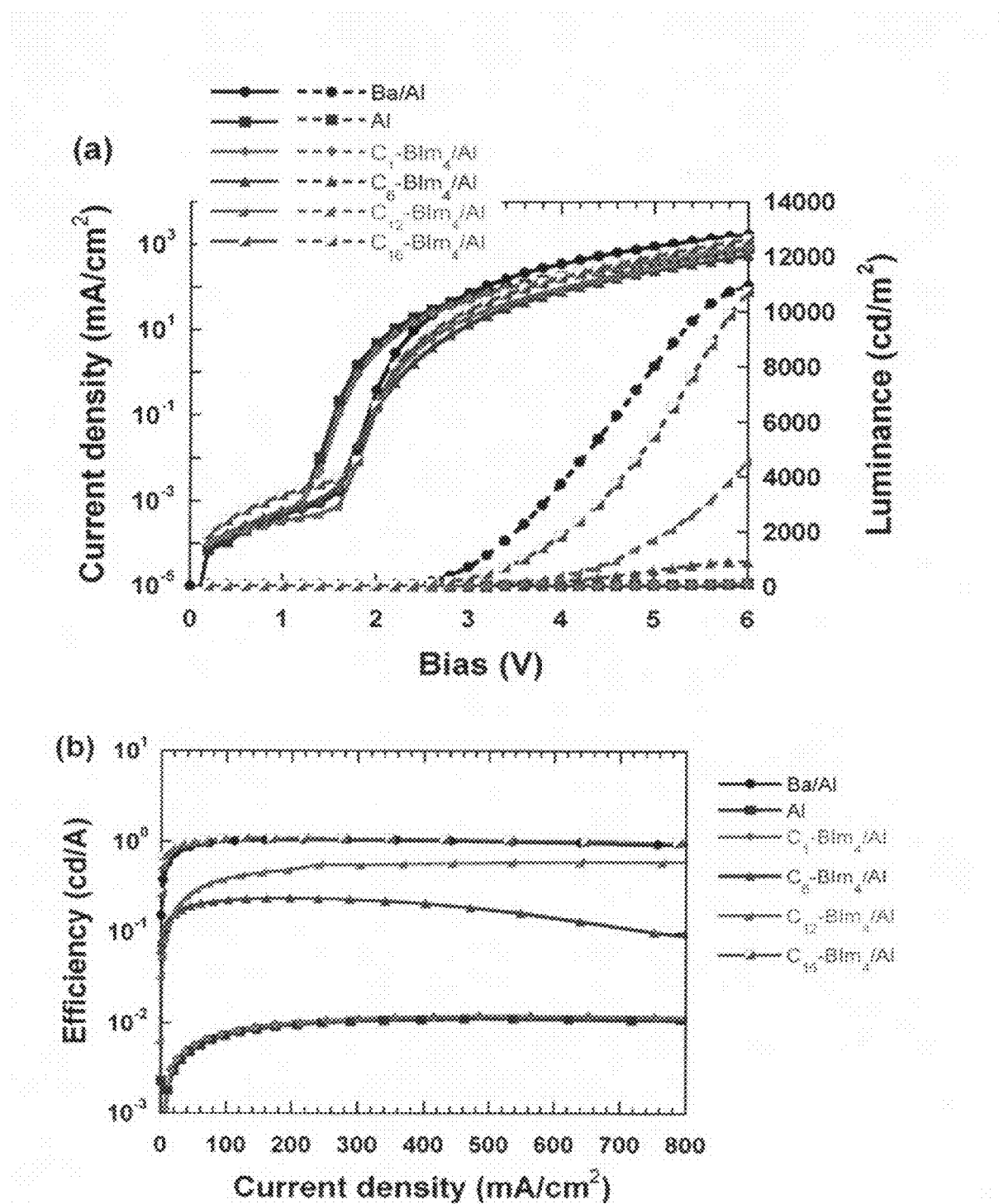
FIG. 3 shows introduction of the zwitterion ETL improves the performance of PLEDs with Al cathodes. (a) J-L-V characteristics and (b) luminousefficiency (cd/A) vs J of ITO/PEDOT:PSS/MEH-PPV/cathode devices with the following cathodes: Ba/Al (black), Al (red), $C_1$—$BIm_4$/Al (green), $C_6$—$BIm_4$/Al (blue), $C_{12}$—$BIm_4$/Al (orange) and $C_{16}$—$BIm_4$/Al (purple).

Shown in FIG. 3a are the current density-luminance-voltage (J-L-V) characteristics of the PLEDs described above as a function of the choice of metal cathode and different zwitterionic and related molecules species. The $C_n$—$BIm_4$ and related molecules layers were deposited from 0.1% solutions in methanol. Table 1 summarizes relevant performance parameters. Most significantly, we note that the maximum power conversion efficiencies of devices that incorporate $C_n$—$BIm_4$ and related molecules layers are higher than that observed when Al is deposited directly atop the emissive layer (0.01 cd/A) as shown in FIG. 3b. This improvement in efficiency becomes more pronounced as the chain length of the alkyl substituent increases: $C_1$—$BIm_4$ (0.01 cd/A), $C_6$—$BIm_4$ (0.24 cd/A), $C_{12}$—$BIm_4$ (0.60 cd/A) to $C_{16}$—$BIm_4$ (1.38 cd/A). Indeed, the value obtained with $C_{16}$—$BIm_4$/Al is comparable to that of Ba/Al devices (1.1.37 cd/A). We also note that the turn-on voltage (Vto), which we define as the point when the emission output reaches 1 cd/m$^2$, also decreases with increasing chain length: $C_1$—$BIm_4$ (2.6 V), $C_6$—$BIm_4$ (2.3 V), $C_{12}$—$BIm_4$ (2.2 V) to $C_{16}$—$BIm_4$ (2.0 V). Compared to the Vto of Al devices (2.6 V), the introduction of the zwitterionic with the shortest alkyl chain, i.e. $C_1$—$BIm_4$, does not change Vto. There is little difference in the Vto values of $C_{16}$—$BIm_4$/Al and Ba/Al, for which there is a negligible barrier to electron injection.[25] These data unambiguously show that the zwitterionic and related molecules/ compounds in Scheme 1 are effective modifiers of the electron injection and that their molecular features bear a strong influence on the PLED performance.

Table 1 also shows that charged species $[2C_{16}$—$BIm_4]^+ .I^-$/ Al and $[4C_{16}BIm_4]^+ .3I^-$/Ba/Al significantly enhance the device performance, even better than those of Ba/Al cathodes when PFO was used as active layers instead of MEH-PPV.

The current density measurements in FIG. 3a correspond to the net contribution by electrons and holes. One finds the following J values at 6 V: Al (824 mA/cm$^2$), $C_1$—$BIm_4$/Al (865 mA/cm$^2$), $C_6$—$BIm_4$/Al (549 mA/cm$^2$), $C_{12}$—$BIm_4$/Al (765 mA/cm$^2$), $C_{16}$—$BIm_4$/Al (1317 mA/cm$^2$), and Ba/Al (1726 mA/cm$^2$). The higher J value for Al, when compared to $C_6$—$BIm_4$/Al and $C_{12}$—$BIm_4$/Al, suggests that the zwitterionic layer not only acts to improve electron injection but also reduces hole current.

Figure 4:
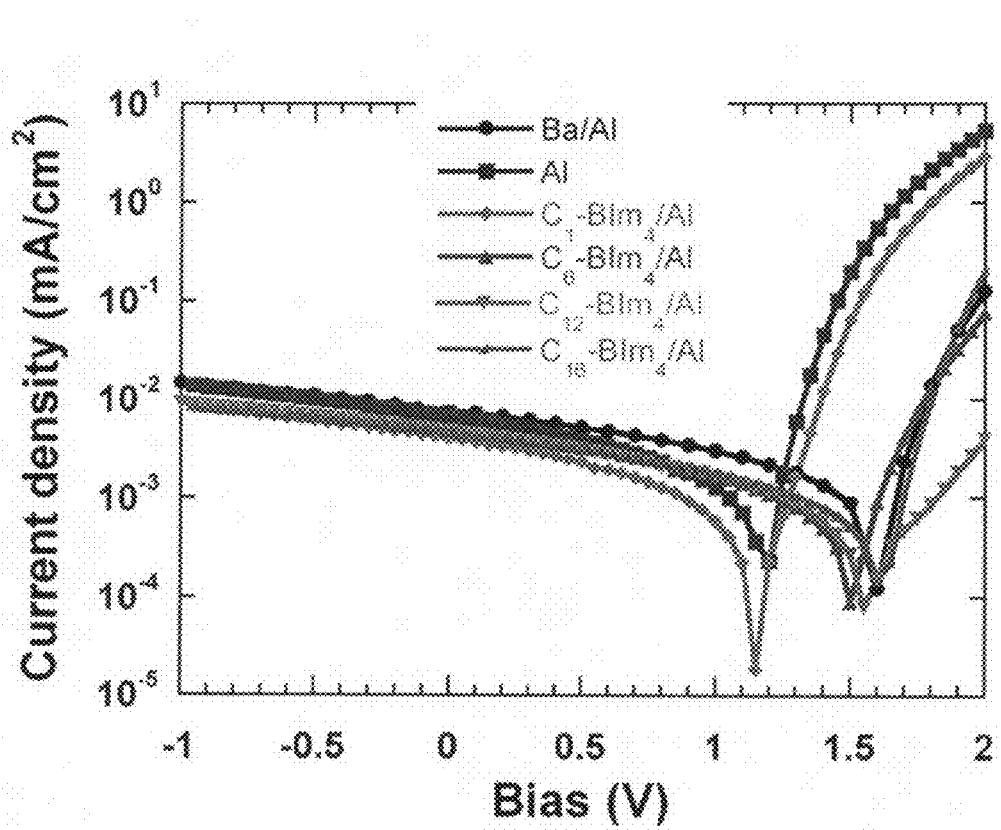
FIG. 4 shows a photovoltaic J-V curves used to determine Voc values as a function of cathode.

Insight into the internal electric fields within PLEDs can be obtained by examination of open circuit voltages (Voc) determined by photovoltaic measurements. In these experiments, an external potential is applied to the device under constant external illumination. The Voc corresponds to the applied bias where the minimum current is measured. Charge carriers experience no internal bias under these conditions. Since the anode is identical for all devices, the Voc is primarily influenced by changes at the cathode. FIG. 4 shows the J-V curves under illumination for the series of devices shown in FIG. 3. We note that the Voc values for $C_1$—$BIm_4$/Al and Al-only devices are similar (~1.20 eV), which closely correlates to the difference in work function between ITO/PEDOT:PSS and Al. For longer alkyl substituents, the Voc values increase with chain length: 1.50 V, $C_6$—$BIm_4$/Al; 1.55 V, $C_{12}$—$BIm_4$/Al; 1.60 V, $C_{16}$—$BIm_4$/Al layer. The latter is indistinguishable from that of Ba/Al cathode devices (1.60 V), which is related to the difference in the work functions of ITO/PEDOT:PSS and Ba. The Voc variations of different cathode devices are fully consistent with the Vto changes, and indicate that the introduction of $C_n$—$BIm_4$ between Al and MEH-PPV modifies the effective work function of the cathode and thus leads to different built-in potentials. We note at this stage that the information attained thus far is extracted from the phenomenology of device performance and does not account for how the introduction of the zwitterion layers leads to the improvement of performance.

Figure 5:
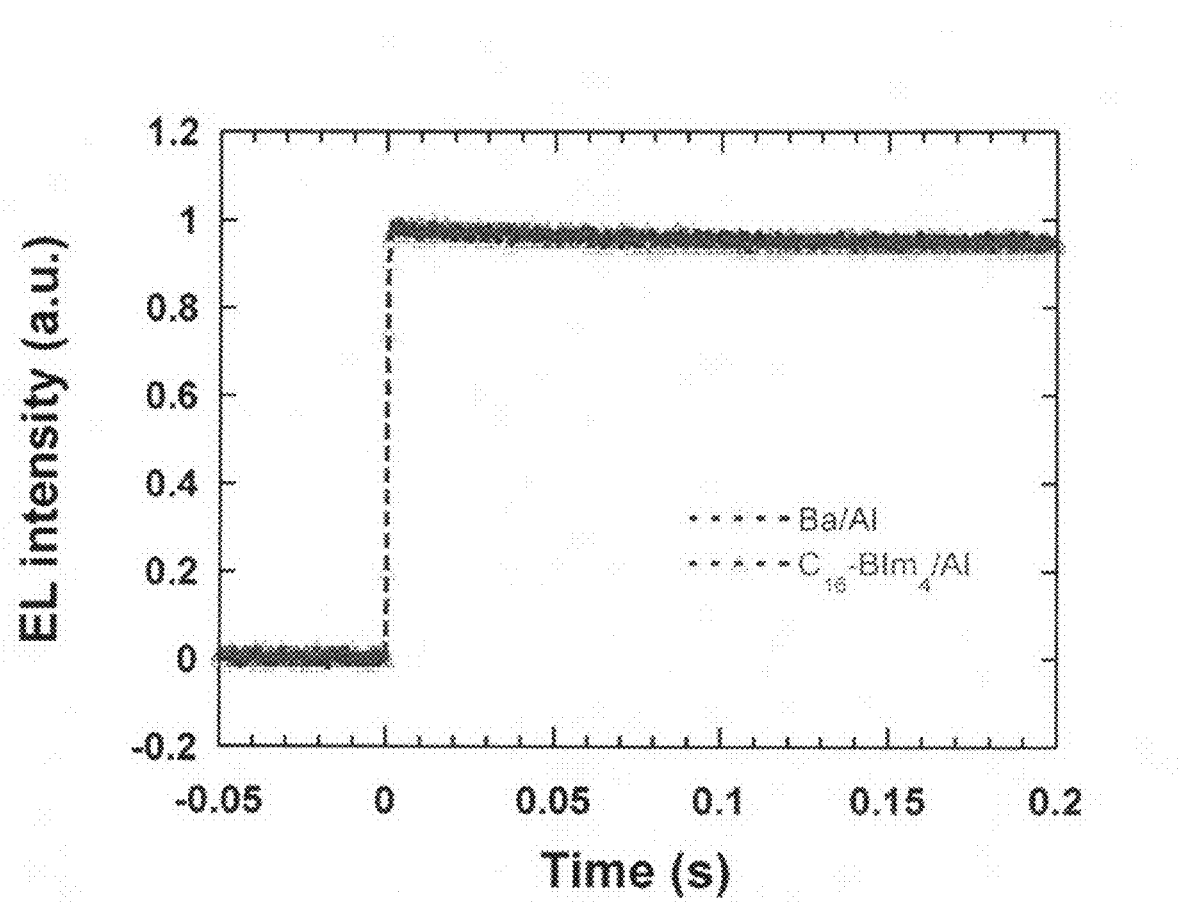
FIG. 5 shows the EL temporal responses at 4 V of ITO/PEDOT:PSS/MEHPPV/$C_{16}$—$BIm_4$/Al (blue triangles) and the control device ITO/PEDOT:PSS/MEH-PPV/Ba/Al (red circles) are similar within the time scale of the experiment.

Several types of ETLs have been shown to be effective, including inorganic and organic Materials.[29-31,36-44,48-53] Injection barriers can be modified via a variety of mechanisms that have been summarized in the literature.[31,32,35,37] For instance, the use of a conjugated polyelectrolyte layer can lead to PLEDs with temporal responses of J and L that are on the order of seconds.[41,42] It is possible to observe under certain circumstances a response time (i.e., the time when J is 50% of its maximum value) of tens of seconds, depending on film thickness and applied bias. Such time scales are consistent with ion migration mediating device performance.[54,55] FIG. 5 shows plots of the electroluminescence (EL) intensity against time for PLEDs with $C_{16}$—$BIm_4$/Al and Ba/Al cathodes. As previously described,[43] measurements involved applying a rectangular voltage pulse. The EL response was registered in the photovoltaic regime by a Si photodiode, which was connected to an oscilloscope. Photocurrent traces were subsequently digitized by the oscilloscope. FIG. 5 shows that within the resolution available with our instrumentation the $C_{16}$—$BIm_4$ layer does not delay the onset of EL. We conclude at this point that, unlike the situation with conjugated polyelectrolytes, there is no need for a large scale redistribution of ions or dipoles for modification of electron injection.

Figure 6:
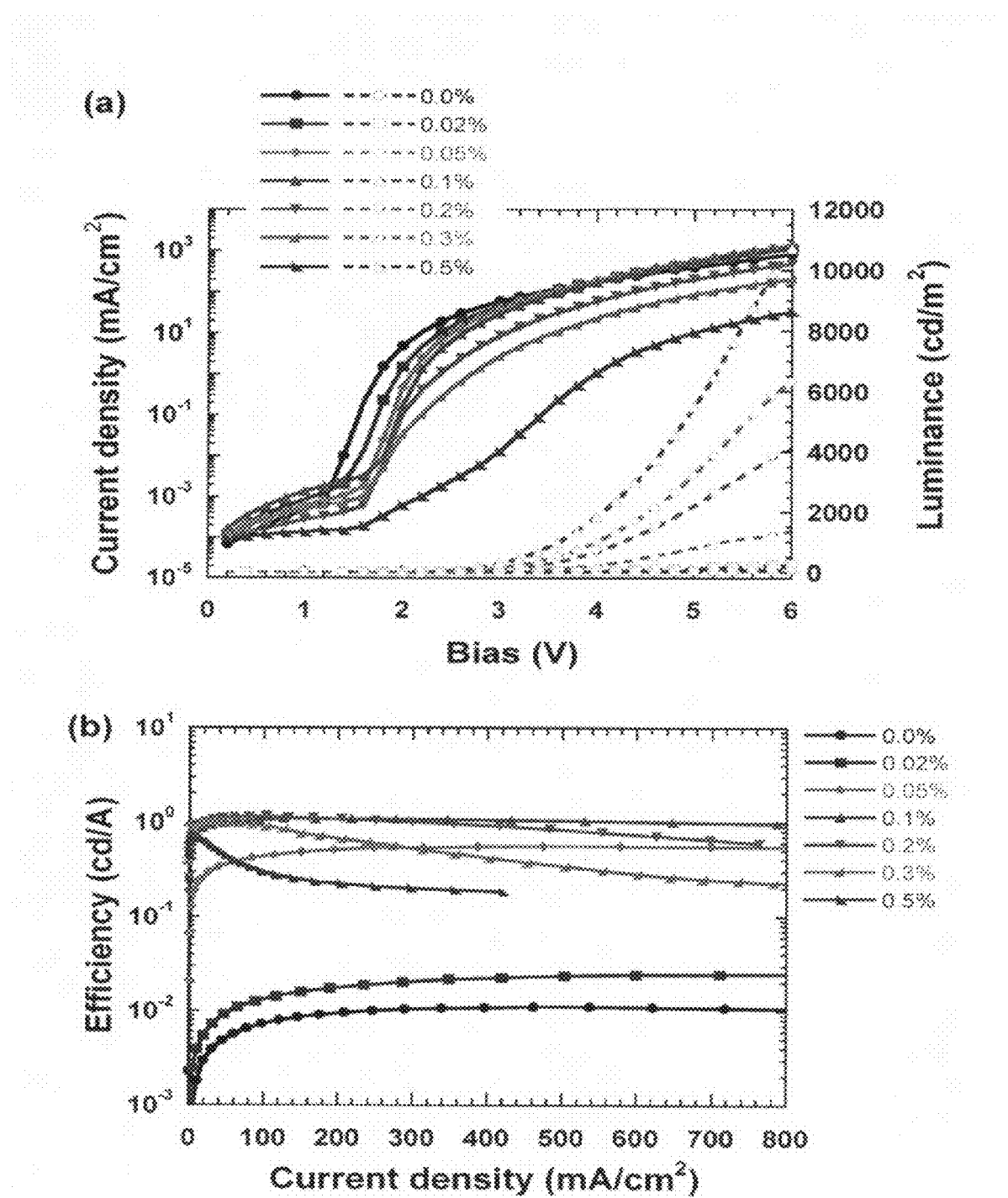
FIG. 6 shows comparison of PLED performance as a function of $C_{16}$—$BIm_4$ loading. (a) J-L-V characteristics and (b) luminous efficiency (cd/A) vs J of ITO/PEDOT:PSS/MEH-PPV/$C_{16}$—$BIm_4$/Al devices as a function of [$C_{16}$—$BIm_4$]: 0.0% (black), 0.02% (red), 0.05% (green), 0.1% (blue), 0.2% (purple), 0.3% (orange) and 0.5% (dark green).

On the basis of the larger improvement in device performance observed when using $C_{16}$—$BIm_4$, we focused on this material to study how the quantity of zwitterion atop MEH-PPV modifies emission and current characteristics. In these studies, the concentration of the methanol solution used to deposit the $C_{16}$—$BIm_4$ layer was varied from 0.02% to 0.5%. All other device fabrication steps were identical to those described previously. The L-J-V curves and electroluminescence efficiencies of the resulting PLEDs displayed in FIG. 6 show that there is an optimal range of concentrations; see also Table 2 for a summary of device performance. Highest efficiencies were obtained when the concentration of $C_{16}$—$BIm_4$ (i.e. [$C_{16}$—$BIm_4$]) is in the range of 0.1 to 0.2%. Lowest Vto values are also observed in this range. However, it is noteworthy that even when one uses a solution with [$C_{16}$—$BIm_4$]) 0.02%, the maximum efficiency (0.05 cd/A) is approximately 5-fold larger than that of Al-only devices (0.01 cd/A). Devices fabricated with higher loadings, i.e. 0.5%, show more unstable behavior, as inferred by the initial downward slope of the dark green curve in FIG. 6b.

It is also informative to focus on the current density characteristics in FIG. 6a. Between 1.5 and 2.0 V, the Al only device shows the highest J values. This is not the case at higher applied biases. For instance, at 6 V devices fabricated with [$C_{16}$—$BIm_4$]) 0.02 (1115 mA/cm$^{-2}$), 0.05 (1336 mA/cm$^{-2}$) and 0.1 (1317 mA/cm$^{-2}$) % solutions show higher J values (relative to Al devices, 824 mA/cm$^{-2}$), while those prepared from [$C_{16}$—$BIm_4$]) 0.2 (484 mA/cm$^{-2}$), 0.3 (206 mA/cm$^{-2}$) and 0.5 (33 mA/cm$^{-2}$) % solutions show lower J values. These data support the previous assessment that the $C_{16}$—$BIm_4$ layer concurrently improves electron injection, as suggested by the lower Vto values, and decreases hole current. The combined action leads to improved charge balance and more efficient devices. The open circuit voltage was also measured as a function of [$C_{16}$—$BIm_4$] by using photovoltaic measurements similar to those shown in FIG. 4. The resulting dependence of Voc on [$C_{16}$—$BIm_4$] is summarized in FIG. 7. One observes a maximum when [$C_{16}$—$BIm_4$]~0.1-0.2%, as the case for the maximum efficiencies in Table 2. We attribute the initial increase of Voc in FIG. 7 to the increase of the built-in potential generated by the difference in effective work functions of $C_{16}$—$BIm_4$/Al and Al cathodes.[25] We highlight that such a scenario requires a preferential alignment of the $C_{16}$—$BIm_4$ molecular dipoles at the Al interface. That the Voc values decrease when [$C_{16}$—$BIm_4$]>~0.2% suggests a loss of $C_{16}$—$BIm_4$ alignment. Additionally, the higher hole current at low bias for the Al-only device is likely related to the higher internal field in the devices. This quantity can be approximated by the difference between the applied bias and the Voc values.

Figure 7:
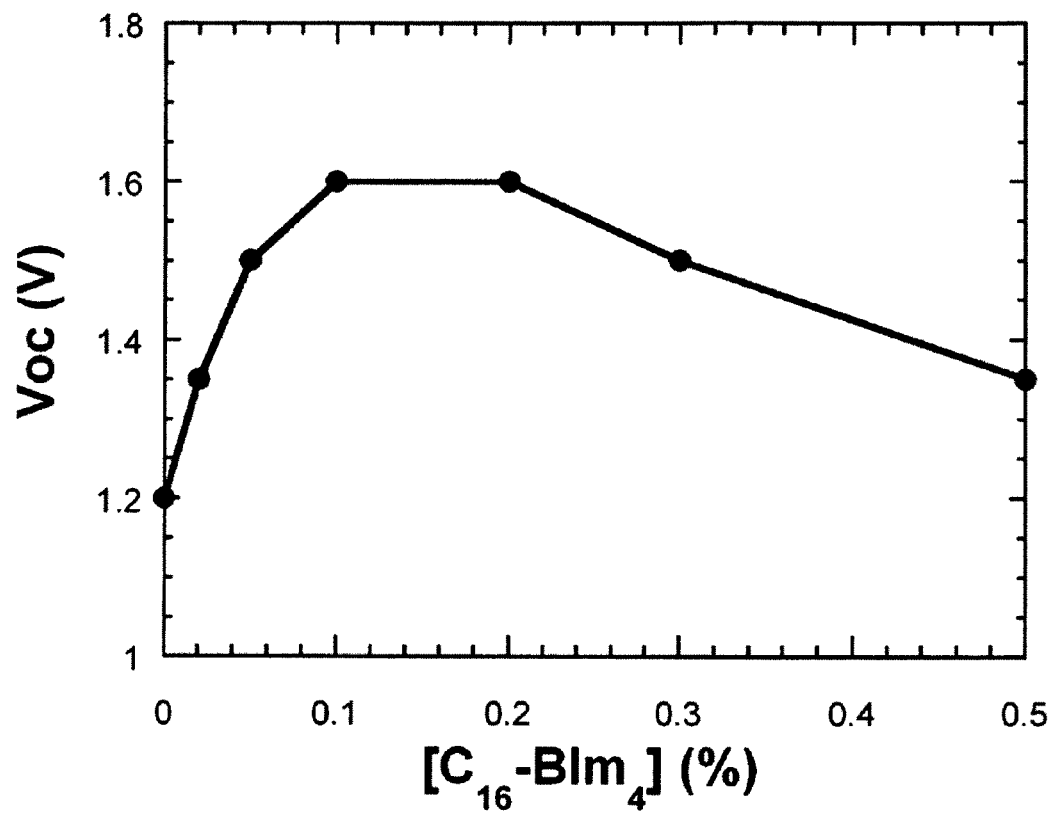
FIG. 7 shows the accumulation of $C_{16}$—$BIm_4$ influences the built-in field of the devices. Plot of Voc against [$C_{16}$—$BIm_4$] in ITO/PEDOT:PSS/MEH-PPV/$C_{16}$—$BIm_4$/Al devices.
Figure 8:
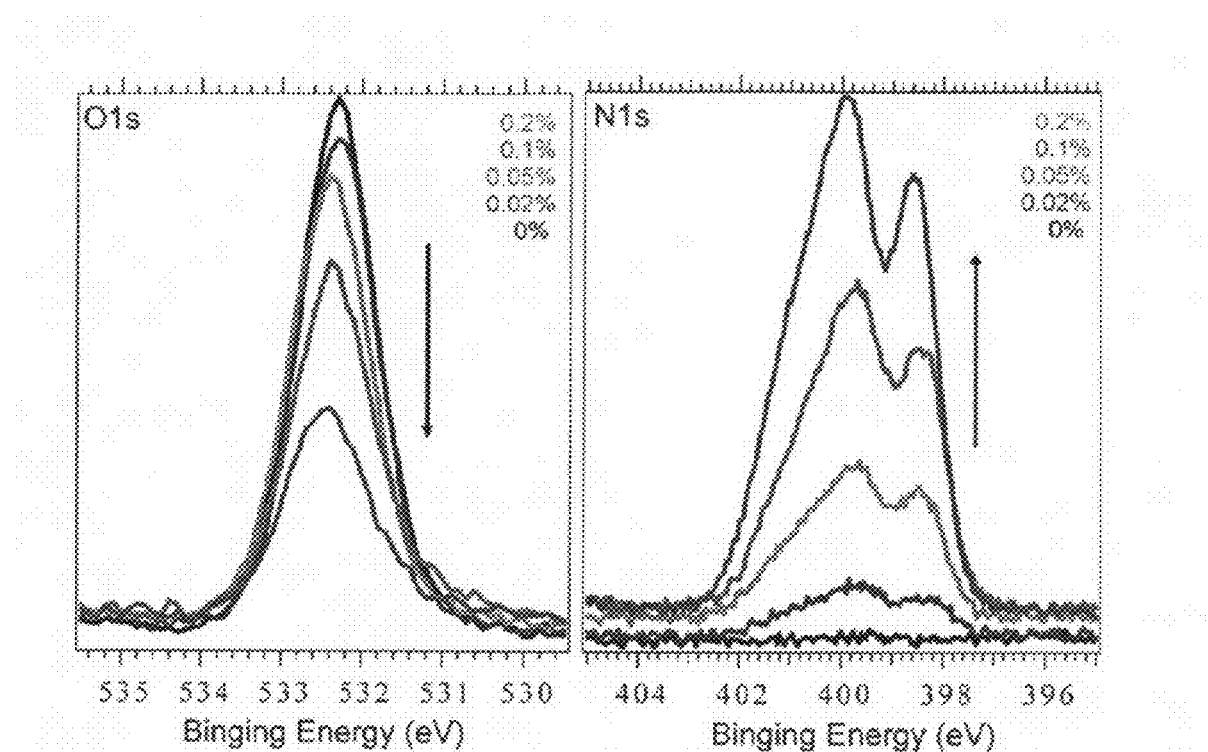
FIG. 8 shows the progressive accumulation of $C_{16}$—$BIm_4$ atop MEH-PPV is demonstrated by the decrease in the intensity of O1s peaks and the increase of N1s peaks. These XPS measurements were made on the area between electrodes as shown in FIG. 1.

Implicit in the discussion of concentration effects is that there is an increase in the accumulation of $C_{16}$—$BIm_4$ with increasing [$C_{16}$—$BIm_4$]. Examination of the device films by profilometry or atomic force microscopy (AFM) reveals no new reproducible features when [$C_{16}$—$BIm_4$]<0.1% (AFM studies with higher [$C_{16}$—$BIm_4$] will be discussed below). These difficulties in characterizing the coverage and thickness of $C_{16}$—$BIm_4$ atop MEH-PPV led us to probing surfaces by using X-ray photoelectron spectroscopy (XPS). XPS data yield elemental composition of the surface to within 5 nm in depth. FIG. 8 shows the XPS spectra that were obtained between the electrodes after device fabrication across the range of $C_{16}$—$BIm_4$ concentrations used in the deposition step. Because of the difference in elemental composition, it is possible to assign the O1s lines to MEH-PPV (from the presence of alkoxy substituents along the polymer backbone), while N1s signatures are indicative of $C_{16}$—$BIm_4$. XPS spectra of films that were treated with $C_{16}$—$BIm_4$ indeed show features corresponding to N1s binding energies, even when [$C_{16}$—$BIm_4$]=0.02%, which are absent when looking at the pristine MEH-PPV film. The progressive increase in N1s intensity and a concomitant decrease in the intensity due to O1s with increasing [$C_{16}$—$BIm_4$] are consistent with the deposition of larger quantities of $C_{16}$—$BIm_4$ on the surface, which attenuate the emission from the underlying MEH-PPV layer. Spectra deposited in the Supporting Information show that deconvolution of the N1s peak reveals contribution from four types of nitrogen, consistent with the molecular structure of $C_{16}$—$BIm_4$. These data confirm that the modification of J-L-V characteristics and Voc values shown in FIGS. 6a and 7 are directly related to changes in the $C_{16}$—$BIm_4$ accumulation.

Thin Film Topography.

Figure 9:
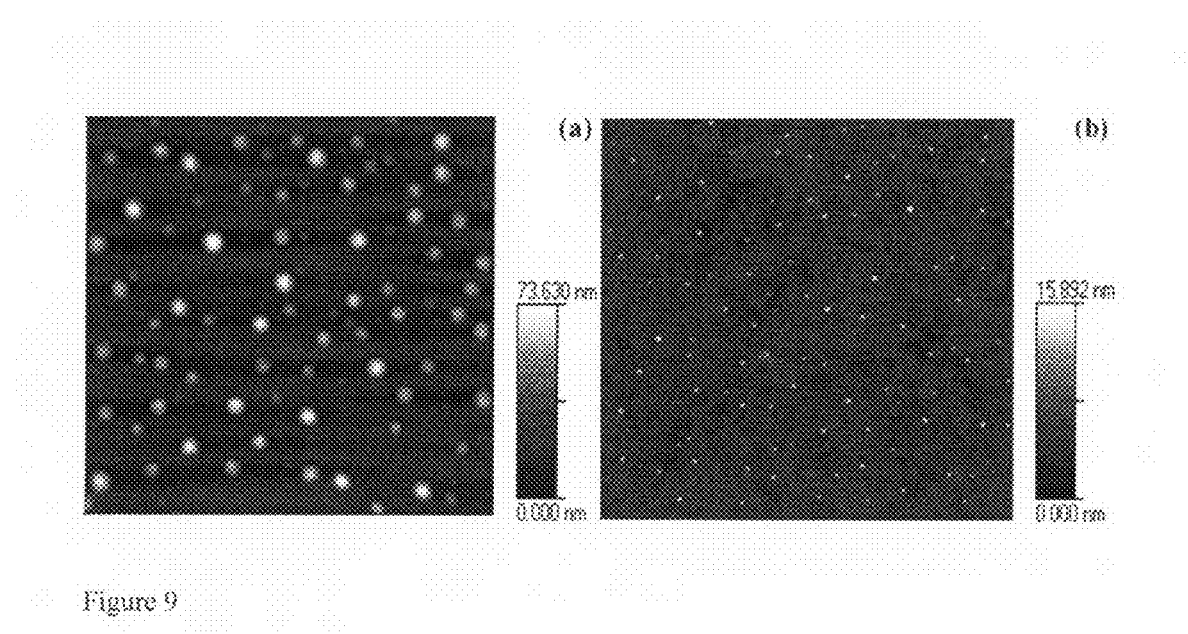
FIG. 9 shows AFM topographies of (a) $C_1$—$BIm_4$ and (b) $C_{16}$—$BIm_4$ deposited on MEH-PPV layers from 0.1% methanol solutions show much larger particulate-like features for the zwitterion with shorter alkyl chain length. Scale: 5 μm×5 μm.

Understanding how the $C_n$—$BIm_4$ layer influences the properties at the metal/organic interface, and particularly the formation mechanism of a preferentially aligned dipole layer, requires examination of the surface structure and possible reconstruction processes as a result of device fabrication. Topographic characteristics after the deposition atop MEH-PPV of 0.1% $C_1$—$BIm_4$ and $C_{16}$—$BIm_4$ in methanol solutions obtained by AFM reveal different morphologies, as shown in FIG. 9. Particulate-like features are observed for both zwitterions, the height of which is larger for $C_1$—$BIm_4$ (>70 nm) than for $C_{16}$—$BIm_4$ (16 nm). Correspondingly, the surface root-mean-square (rms) roughness of 5 μm×5 μm $C_n$—$BIm_4$ on MEH-PPV decreases from ~10 nm for $C_1$—$BIm_4$ to ~1 nm for $C_{16}$—$BIm_4$. Measurements of the total film thickness for the complete PEDOT:PSS/MEH-PPV/$C_{16}$—$BIm_4$ structure by AFM and profilometry show that the $C_{16}$—$BIm_4$ addition gives rise to no observable thickness increase. We also find (Supporting Information) that zwitterions with intermediate chain lengths provide a continuum of sizes for the raised features in the two extremes in FIG. 9, with the shorter chain lengths giving rise to rougher surfaces. These different topographies indicate that the pendant alkyl chain is an important structural handle in improving materials performance by increasing the adhesion/wetting to the underlying hydrophobic MEH-PPV layer.

Figure 10:
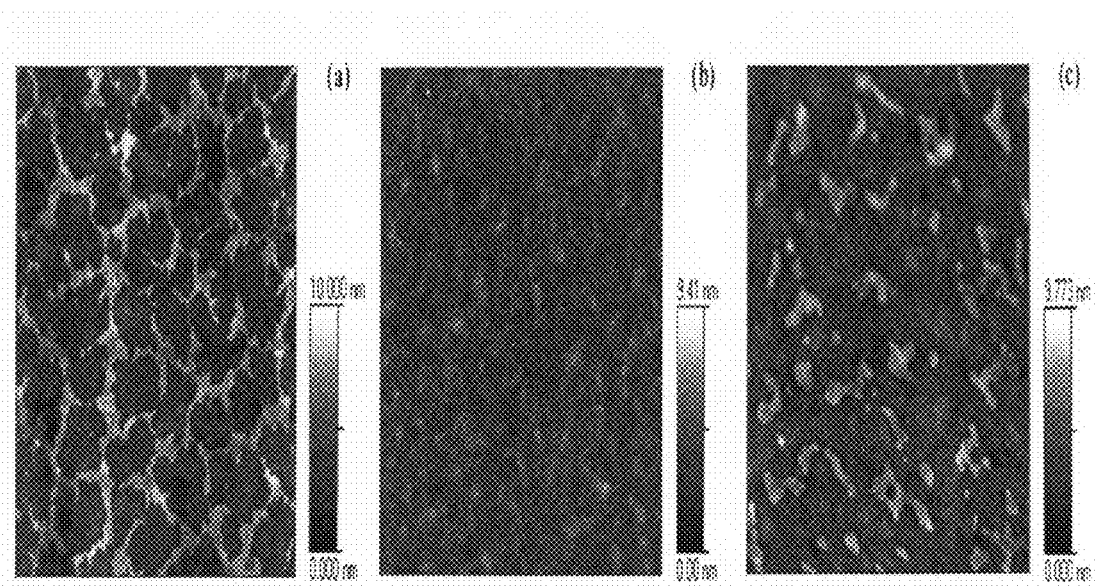
FIG. 10 shows the topographic AFM images of $C_{16}$—$BIm_4$ on MEH-PPV layer deposited from a 0.2% solution (a) before Al evaporation, (b) after Al evaporation, <100 μm from the electrode, and (c) after Al evaporation, >5 mm from the electrode. Scale: 5 μm×5 μm.

It should be mentioned that the patterns shown in FIG. 9b are highly variable in terms of spot density, heights and average distribution throughout the surface, even when extreme care is taken to reproduce deposition conditions. Increasing [$C_{16}$—$BIm_4$] to 0.2% leads to the formation of the features shown in FIG. 10a, where connected and continuous raised features are observed throughout the surface. These features are easily reproducible, and for this reason we will focus subsequent discussion on the changes that occur on these surfaces. Based on FIG. 10a, it is difficult to anticipate homogeneous electron injection from an Al cathode atop this layer. To resolve this disparity, topographic features were measured after the deposition of Al at distances close to (<100 µm, FIG. 10b) and far from (~5 mm, FIG. 10c) the metal edge. We find that the surface is smooth and homogeneous adjacent to the electrode, unlike FIG. 10a. Further away one finds features reminiscent of the topography obtained immediately after deposition of the zwitterion. Combining the results indicates that the deposition of Al planarizes the $C_{16}$—$BIm_4$ layer and provides a homogeneous contact. The distance dependence leads us to believe that local heating upon metal deposition thermally anneals $C_{16}$—$BIm_4$, leading to local melting and improved conformity between the layers.

Surface Potential Characterization by Scanning Kelvin Probe Force Microscopy.

Thus far, it has been established that spin coating $C_{16}$—$BIm_4$ followed by deposition of Al leads to smooth layers adjacent to the electrode and an improvement of PLED efficiency by reduction of electron injection barriers and a better balance of charge carriers. If introduction of the zwitterion leads to the formation of an aligned dipole layer, then this surface should exhibit a higher potential when compared to MEH-PPV, which lacks highly polar chemical functionalities. To examine whether this scenario is reasonable, the changes in surface potential were probed using scanning Kelvin probe force microscopy (SKPFM). This technique probes the local potential within fine features and has been successfully used for investigating the internal electric field distribution in light-emitting electrochemical cells[56,57] and heterojunctions in organic photovoltaic devices.[58-61] In our experiments, we used platinum-iridium coated Si probes with a resonant frequency around 83 kHz. Topographic features were first recorded in tapping mode, followed by the surface potential scan at a fixed lift height of 50 nm above the surface, i.e. the interleave scan.[62] As the scanning tip approaches the sample, an electric field is generated due to the differential chemical potentials between the tip and the organic layer. The backing voltage applied to the tip to nullify this field provides a relative measure of the surface potential.

Figure 11:
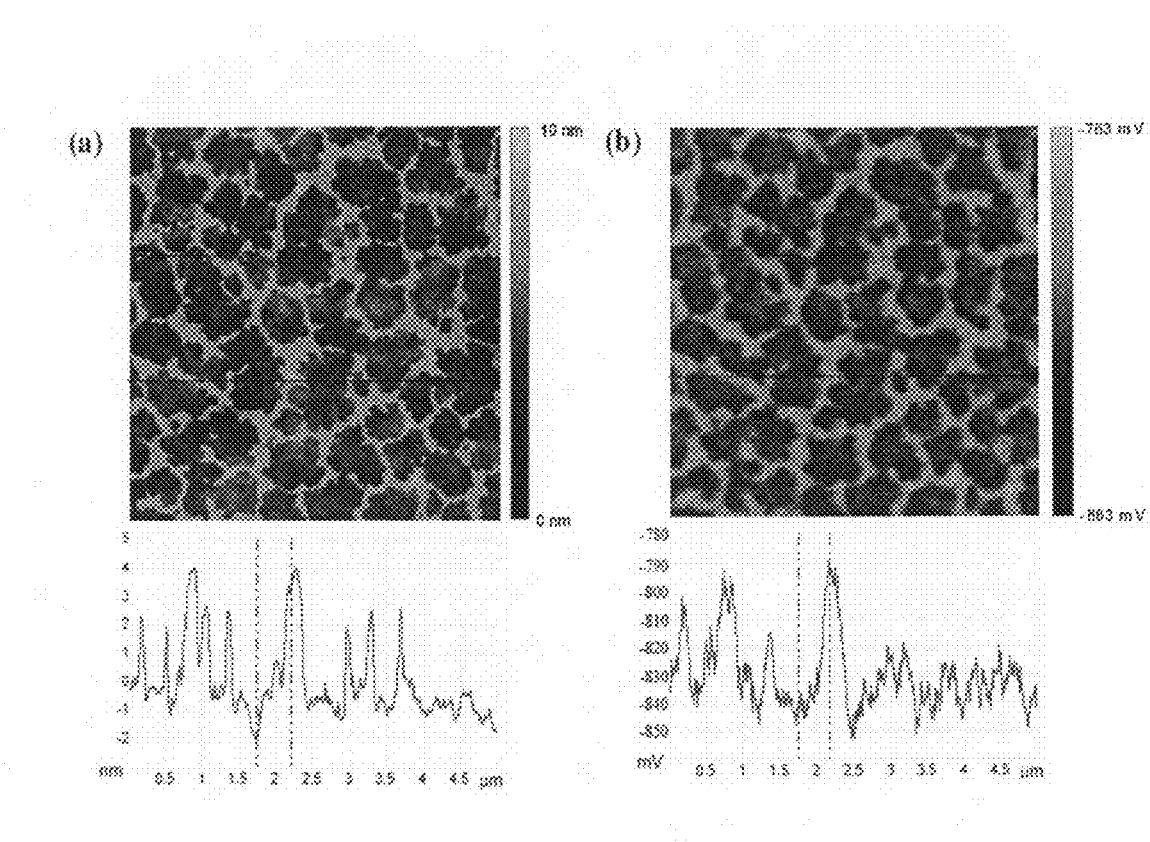
FIG. 11 shows a SKPFM analysis of $C_{16}$—$BIm_4$ atop MEH-PPV. (a) Topographic and (b) surface potential images of MEH-PPV/$C_{16}$—$BIm_4$ film surface. Scale: 5 μm×5 μm. The concentration of the $C_{16}$—$BIm_4$ solution was 0.2%.

FIG. 11a shows the surface topography of $C_{16}$—$BIm_4$ deposited from a 0.2% solution on the MEH-PPV layer before electrode evaporation as measured by using the modified tip probes. One observes connected and continuous raised features with average heights of 2-5 nm as previously shown in FIG. 10a. The background features in this image are typical of the MEH-PPV film. The results from the interleave scans across the same area as in FIG. 11a show that the surface potential image is closely correlated to the topographic image, as shown in FIG. 11b. From the cross sectional analysis, the potential at the raised features is approximately 50 mV higher than that measured at the base.

Figure 12:
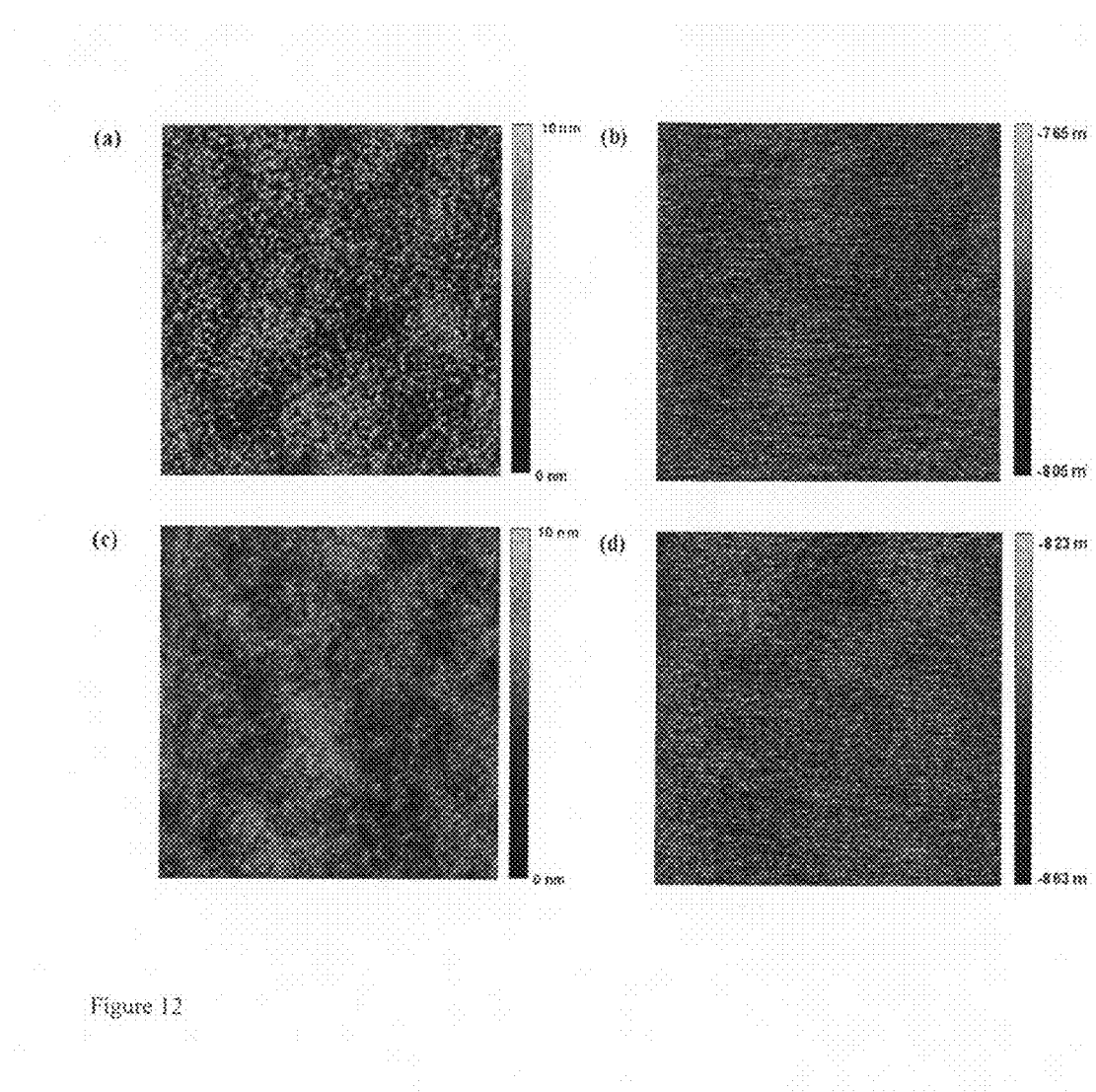
FIG. 12 shows the concentration of the $C_{16}$—$BIm_4$ solution was 0.2%. Topographic images (a and c) adjacent to the electrode and surface potential images (b and d) of MEH-PPV (a and b) and MEH-PPV/$C_{16}$—$BIm_4$ (c and d). Scale: 2 μm×2 μm.

FIGS. 12a and 12b show the topography and surface potential, respectively, from the MEH-PPV/$C_{16}$—$BIm_4$ surface in a device at a site adjacent to the electrode, while FIGS. 12c and 12d provide the corresponding data from an Al-only device, i.e. direct imaging of the MEH-PPV layer. The MEH-PPV/$C_{16}$—$BIm_4$ surface is slightly rougher, with a root-meansquare (rms) roughness of 0.95 nm, when compared to MEHPPV (rms: 0.62 nm). No major features are observed in the scan of the potentials. Significantly, FIGS. 12b and 12d were measured under the same conditions and using the same tip. It is therefore possible to make a relative comparison of average surface potential between MEH-PPV (~−840 mV) and MEH-PPV/$C_{16}$—$BIm_4$ (~−780 mV), which corresponds to a difference of approximately 60 mV. We recognize that we have not probed the environment immediately beneath the Al electrode. Nonetheless, the SKPFM results are fully consistent with the spontaneous formation of a well-aligned dipole layer upon deposition of the metal.

SUMMARY DISCUSSION AND CONCLUSIONS

We have disclosed a new class of materials based on zwitterionic small molecules of the type Cn-$BIm_4$ and related molecules that effectively modulate charge injection and balance in organic optoelectronic devices. A trivial synthesis is provided that takes advantage of commercially available starting materials. The metrical parameters obtained from single crystal diffraction studies of the methylated derivative $C_1$—$BIm_4$ were used to estimate a molecular dipole moment of 14 D within the zwitterionic core common to all $C_n$—$BIm_4$ derivatives. Based on evaluation of PLEDs with a general architecture ITO/PDOT:PSS/MEH-PPV/cathode, it is found that the inclusion of $C_n$—$BIm_4$ between the emissive layer and the electrode leads to substantial improvement in the luminance efficiencies when using Al. The length of the quaternizing alkyl chain is critical for achieving good performance and provides an important structural handle for consideration in future optimization studies. For example, $C_1$—$BIm_4$/Al leads to a marginal improvement compared to Al, and the $C_{16}$—$BIm_4$/Al combination approaches the efficiency observed for Ba/Al, for which there is essentially ohmic contact and negligible barrier for electron injection into MEH-PPV. This process provides a remarkably simple strategy for circumventing the use of unstable low workfunction metals and to obtain charge balance and high electroluminescence efficiency in the device.

AFM examination of topographic features reveals incomplete coverage of the MEH-PPV underlayer when the $C_n$—$BIm_4$ compounds are deposited from solution. However, the heights of the domains achieved with the longer alkyl chains are smaller, which we interpret as indicative of better interactions with the hydrophobic substrate. Nonetheless, even for $C_{16}$—$BIm_4$ one find inhomogenous features that would not be expected to improve electron injection throughout the cathode surface. We find that the MEH-PPV/$C_{16}$—$BIm_4$ surface becomes flat and homogeneous after deposition of Al. This flattening process is more pronounced closest to the electrode surface, which we take to imply that it is caused by a local heating effect when Al transfers kinetic energy to the substrate. This surface reconstruction process induced by a device fabrication step is an interesting observation that may have general consequences when trying to understand interfacial effects within thin-film organic devices.

Absence of a temporal response for electroluminescence, in contrast to the situation as the case of conjugated polyelectrolyte layers, together with the variation in Voc values and Kelvin probe measurements is consistent with the formation of an aligned dipole layer at the $C_{16}$—$BIm_4$/Al interface that causes a shift in the vacuum level and effectively reduces the electron injection barrier. The Voc has been regarded as an estimate of the built in potential across the device. Therefore, with the addition of $C_{16}$—$BIm_4$ the built-in field is increased while the electron injection barrier is decreased. The larger built-in field in the $C_{16}$—$BIm_4$/Al device is reflected in the J-V characteristics at low biases where the Al device has a larger current density due to its larger internal field (applied field-built-in field).

Figure 13:
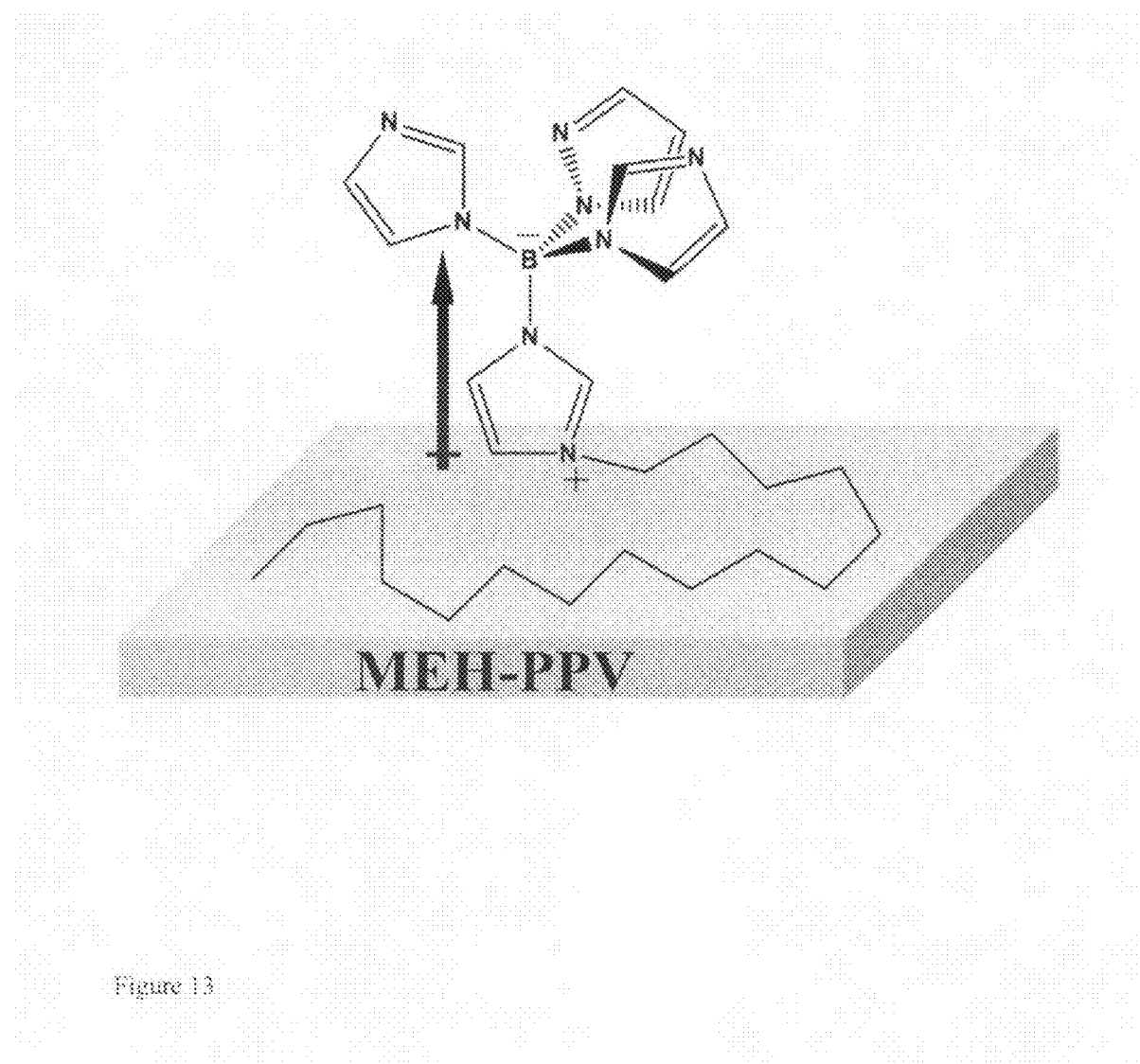
FIG. 13 shows a schematic of the proposed interaction of the alkyl chain with MEH-PPV and concomitant alignment of the $C_{16}$—$BIm_4$ dipole orthogonal to the surface

Based on the discussion above, we propose that the final organization of $C_{16}$—$BIm_4$ molecules is as shown in FIG. 13, with the alkyl chain in preferential contact with the hydrophobic MEH-PPV surface. Such a disposition not only forces the intrinsic molecular dipole orthogonal to the surface but also leads to the correct orientation of dipoles to increase the effective work function of the cathode. Note that FIG. 13 is meant to illustrate the general direction of the dipole relative to the surface and its relationship to the molecular structure;

it is not meant to serve as an accurate depiction of all possible molecular binding modes and interactions with the surface. It is also interesting to note that the electrostatic repulsion between coaligned dipoles is compensated by the nonpolar hydrophobic contacts.

EXPERIMENTAL SECTION

General Details

Sodium tetrakis(1-imidazolyl)borate, iodomethane, 1-iodohexane, 1-iodododecane and 1-iodohexadecane were purchased from Aldrich-Sigma and used as received. 1H and $^{13}$C NMR spectra were collected on Varian Inova 400 MHz spectrometers. Mass spectroscopy and elemental analysis were performed in the UC Santa Barbara Mass Spectrometry Lab and elemental analysis center.

General Synthetic Procedures.

NaBIm$_4$ (302 mg, 1 mmol) was dissolved in 100 mL of DMF (dimethylformamide). To the solution, iodoalkane (1 mmol) was added. The mixture solution was stirred for 24 h at room temperature. After the solvent was removed via vacuum evaporator, the residual was purified using a silica-gel column with 10% methanol in chloroform as the eluent to give white uncharged zwitterions $C_n$—BIm$_4$ (yield: 40%).

Syntheses of $C_{16}$—BIm$_4$, $[2C_{16}$—BIm$_4]^+.I^-$, and $[4C_{16}$—BIm$_4]^{3+}.3I^-$ NaBIm$_4$ (302 mg, 1 mmol) was dissolved in 100 mL of DMF (dimethylformamide). To the solution, neat 1-iodohexadecane (352 mg, 1 mmol) was added. The mixture solution was stirring for 24 hr at room temperature. After the solvent was removed via use of a vacuum evaporator, the residue was purified using a silica-gel column with 10% methanol in chloroform as the eluent to give a waxy white powder $C_{16}$—BIm$_4$ (174 mg, yield: 48%) and $[2C_{16}$—BIm$_4]^+.I^-$ (245 mg, 29%).

$C_{16}$—BIm$_4$: $^1$H NMR (CDCl$_3$, 400 MHz) δ 8.29 (s, 1H), 7.25 (s, 1H), 7.17 (s, 3H), 7.05 (s, 1H), 7.04 (s, 3H), 6.75 (s, 3H), 4.13 (t, J=7.4 Hz, 2H), 1.80 (m, 2H), 1.2× (m, 2H), 1.20 (m, 24H), 0.82 (t, J=6.8 Hz, 3H) ppm; $^{13}$C NMR (CDCl$_3$, 100 MHz) δ 140.18, 137.40, 130.58, 124.83, 122.10, 120.93, 50.00, 32.07, 30.47, 29.83, 29.81, 29.72, 29.63, 29.52, 29.47, 29.02, 26.44, 22.85, 14.31 ppm. MS (ESI) m/z: 505.40 (calcd. 505.39 for [M+H]$^+$). Anal. Calcd. for C$_{18}$H$_{45}$BN$_8$C, 66.66; H, 8.99; N, 22.21. found C, 65.90; H, 9.07; N, 22.27.

$[2C_{16}$—BIm$_4]^+.I^-$. $^1$H NMR (CDCl$_3$, 400 MHz) δ 9.09 (s, 2H), 7.30 (s, 2H), 7.26 (s, 4H), 7.24 (s, 2H), 6.99 (s, 2H), 6.87 (s, 2H), 4.39 (t, J=7.6 Hz, 4H), 1.90 (m, 4H), 1.32 (m, 4H), 1.24 (m, 48H), 0.87 (t, J=6.8 Hz, 6H) ppm; $^{13}$C NMR (CDCl$_3$, 100 MHz) δ 140.18, 138.68, 131.92, 123.71, 123.09, 120.60, 50.81, 32.07, 30.47, 29.83, 29.81, 29.72, 29.63, 29.52, 29.47, 29.02, 26.44, 22.85, 14.31 ppm. MS (ESI) m/z: 729.66 (calcd. 730.97 for [M-I+H]$^+$).

NaBIm$_4$ (302 mg, 1 mmol) was dissolved in 100 mL of DMF (dimethylformamide). To the solution, neat 1-iodohexadecane (1.408 g, 4 mmol) was added. The mixture solution was stirring for 24 hr at room temperature. After the solvent was removed via use of a vacuum evaporator, the residue was washed using water and then hexane to give a waxy white powder $[4C_{16}$—BIm$_4]^{3+}.3I^-$ (1.4 g, yield: 95%). $[4C_{16}$—BIm$_4]^{3+}.3I^-$: $^1$H NMR (CDCl$_3$, 400 MHz) δ 9.16 (s, 4H), 8.00 (s, 4H), 7.36 (s, 4H), 4.23 (t, J=7.9 Hz, 8H), 2.03 (m, 8H), 1.35 (m, 8H), 1.24 (m, 96H), 0.87 (t, J=7.0 Hz, 12H) ppm; $^{13}$C NMR (CDCl$_3$, 100 MHz) δ 140.94, 124.05, 123.86, 51.01, 32.12, 29.90, 29.87, 29.84, 29.74, 29.68, 29.57, 29.18, 26.80, 22.90, 14.34 ppm. MS (ESI) m/z: 1434.02 (calcd. 1435.67 for [M-I+H]$^+$).

Syntheses of $C_1$—BIm$_4$

NaBIm$_4$ (302 mg, 1 mmol) was dissolved in 100 mL of DMF (dimethylformamide). To the solution, 62 μL of iodomethane (1 mmol) was added dropwise. The solution was stirred for 24 hr at room temperature. After the removal of DMF, the residue was purified by chromatography using a silica-gel column as the support and methanol as the eluent. A white powder (132 mg) was obtained in 45% yield. $^1$H NMR (CD$_3$OD, 400 MHz) δ 8.41 (s, 1H), 7.62 (s, 1H), 7.54 (s, 3H), 7.32 (s, 1H), 7.23 (s, 3H), 7.08 (s, 3H), 3.93 (s, 3H) ppm; $^{13}$C NMR (CD$_3$OD, 100 MHz) δ 143.60, 143.14, 131.99, 130.55, 127.68, 125.87 ppm. MS (ESI): [M+H]$^+$295.16 (calculated 295.15). Elemental anal.: calcd for C$_{13}$H$_{15}$BN$_8$C, 53.09; H, 5.14; N, 38.10. found C, 52.96; H, 5.28; N, 38.14.

$C_6$—BIm$_4$, $C_{10}$—BIm$_4$, and $C_{12}$—BIm$_4$ were similarly made. Other Zwitterionic materials, as disclosed above, can also be made in a similar fashion.

1-(3-Hexylimidazolyl)-tris(1-imidazolyl)borate $C_6$—BIm$_4$: $^1$H NMR (CD$_3$OD, 400 MHz) δ 8.22 (s, 1H), 7.28 (s, 1H), 7.24 (s, 3H), 7.07 (s, 1H), 7.07 (s, 3H), 7.06 (s, 3H), 4.15 (t, J=7.4 Hz, 3H), 1.84 (t, J=6.6 Hz, 2H), 1.27 (s, broad, 6H), 0.84 (t, J=6.6 Hz, 3H) ppm; $^{13}$C NMR (CD$_3$OD, 100 MHz) δ 140.14, 137.32, 130.38, 124.79, 122.31, 121.00, 50.23, 31.10, 30.37, 26.09, 22.51, 14.06 ppm. MS (ESI): [M+H]$^+$ 365.24 (calculated 365.26). Elemental anal.: calcd for C$_{18}$H$_{25}$BN$_8$C, 59.35; H, 6.92; N, 30.76. found C, 59.13; H, 7.01; N, 30.87.

1-(3-Dodecylimidazolyl)-tris(1-imidazolyl)borate $C_{12}$—BIm$_4$: $^1$H NMR (CDCl$_3$, 400 MHz) δ 8.46 (s, 1H), 7.76 (s, 3H), 7.26 (s, 1H), 7.23 (s, 3H), 7.07 (s, 1H), 6.89 (s, 3H), 4.30 (s, J=7.4 Hz, 2H), 1.87 (t, J=6.8 Hz, 2H), 1.32 (t, J=6.8 Hz, 2H), 1.24 (s, broad, 14H), 0.87 (t, J=6.8 Hz, 3H) ppm; $^{13}$C NMR (CDCl$_3$, 100 MHz) δ 140.23, 137.23, 130.69, 125.02, 122.24, 120.99, 50.25, 32.11, 31.29, 29.81, 29.76, 29.66, 29.54, 29.51, 29.06, 26.77, 22.89, 14.33 ppm. MS (ESI): [M+H]$^+$ 449.32 (calculated 449.33). Elemental anal.: calcd for C$_{24}$H$_{37}$BN$_8$C, 64.28; H, 8.32; N, 24.99. found C, 64.17; H, 8.52; N, 25.22.

1-(3-Hexadecylimidazolyl)-tris(1-imidazolyl)borate $C_{16}$—BIm$_4$: $^1$H NMR (CDCl$_3$, 400 MHz) δ 8.29 (s, 1H), 7.25 (s, 1H), 7.17 (s, 3H), 7.05 (s, 1H), 7.04 (s, 3H), 6.75 (s, 3H), 4.13 (t, J=7.4 Hz, 2H), 1.80 (m, 2H), 1.24 (m, 2H), 1.20 (m, 24H), 0.82 (t, J=6.8 Hz, 3H) ppm; $^{13}$C NMR (CDCl$_3$, 100 MHz) δ 140.18, 137.40, 130.58, 124.83, 122.10, 120.93, 50.00, 32.07, 30.47, 29.83, 29.81, 29.72, 29.63, 29.52, 29.47, 29.02, 26.44, 22.85, 14.31 ppm. MS (ESI) m/z: 505.40 (calcd 505.39 for [M+H]$^+$). Anal.: calcd for C$_{18}$H$_{45}$BN$_8$C, 66.66; H, 8.99; N, 22.21. found C, 65.90; H, 9.07; N, 22.27.

Fabrication and Measurements of PLEDs.

Devices were fabricated on prepatterned indium-tin oxide (ITO) with a sheet resistance of 10-20 Ω/square. The ITO substrate was cleaned under ultrasonic conditions with detergent, deionized water, acetone and isopropanol consecutively. The cleaned ITO was treated in UV ozone for 40 min. On the top of ITO, the aqueous dispersion of poly(3,4-ethylenedioxythiophene):polystyrene sulfonic acid (PEDOT:PSS, Baytron P 4083, Bayer AG) was spin-cast to form a layer of film with thickness of 60 nm. The formed PEDOT:PSS films were baked at 180° C. for 10 min inside a nitrogen filled glovebox. On the top of ITO/PEDOT:PSS, 0.6% (6 mg/mL) of MEH-PPV (poly[2-methoxy-5-(2'-ethylhexyloxy)-1,4-phenylene vinylene], 70 nm) or 4 mg/mL of PFO (poly 9,9'-dioctylfluorene) film was spin-casted in toluene solution, then a thin layer of zwitterionic material i.e. $C_{16}$—BIm$_4$ was added using its methanol solution. Finally, a 100 nm thick aluminum capping layer was thermally deposited by vacuum evaporation through a mask at a base pressure below $1 \times 10^{-6}$ Torr. The spin-casting of EL layers and the device performance tests were carried out within a glovebox with nitrogen circulation. The control devices were fabricated and tested in the same conditions. Current density-voltage-luminance (J-V-L) characteristics were measured with a computerized Keithley 2602 Source measure unit and a multimeter coupled with a photodiode.

X-ray Photoemission Spectroscopy Measurement.

The XPS analysis chamber was equipped with a hemispherical electron energy analyzer (Kratos Ultra Spectrometer) and was maintained at $1 \times 10^{-9}$ Torr. The XPS was measured using monochromatized Al Kα (hv=1486.6 eV) excitation with an angle of 35°, and the electron energy analyzer was operated at constant pass energy of 20 eV with 90° (for XPS). To minimize possible influence by exposure to air, the films were then transferred from the $N_2$-atmosphere drybox to the analysis chamber inside an air-free holder. Subsequently, all samples were kept inside a high-vacuum chamber overnight to remove solvent.

Surface Potential Measurements Scanning Kelvin Probe Force Microscopy (SKPFM).

The samples for SKPFM were prepared as described above. SKPFM measurements were carried out on Dimension ICON scanning probe microscope coupled with Nanoscope V controller (Veeco Instruments). For all these surface potential measurements, either doped Si (model FESP) or platinum-iridium coated Si probes (model SCM-PIT from Veeco Probes) with a resonant frequency around 83 kHz were used. SKPFM measurement employs the so-called lift-mode, a two-pass scanning technique. In the first pass, the surface topographical data is acquired in tapping-mode. In the second pass, a rescan of the same line is done by lifting the tip off 50 nm above the profilerecorded in the first pass while surface potential data is determined. During the rescan, the ac voltage that drives the tapping piezo is turned off; instead, an ac voltage of 500 mV in amplitude is applied to the conductive tip to cause it to oscillate in the electric field that arises from the contact potential, essentially the work function difference between the sample and tip. The electric field is nullified by applying a dc voltage to the tip such that the oscillation amplitude drops to zero; at this point, the dc voltage equals the contact potential. As the tip remains unchanged during the scan, the potential map reflects sample surface potential variations.

References (1) Tang, C. W.; Vanslyke, S. A. Appl. Phys. Lett. 1987, 51, 913-915.
(2) Burroughes, J. H.; Bradley, D. D. C.; Brown, A. R.; Marks, R. N.; Mackay, K.; Friend, R. H.; Burns, P. L.; Holmes, A. B. Nature 1990, 347, 539-541.
(3) Kraft, A.; Grimsdale, A. C.; Holmes, A. B. Angew. Chem., Int. Ed. 1998, 37, 402-428.
(4) Sirringhaus, H.; Tessler, N.; Friend, R. H. Science 1998, 280, 1741-1744.
(5) Dimitrakopoulos, C. D.; Malenfant, P. R. L. AdV. Mater. 2002, 14, 99-117.
(6) Walzer, K.; Maennig, B.; Pfeiffer, M.; Leo, K. Chem. ReV. 2007, 107, 1233-1271.
(7) Tang, C. W. Appl. Phys. Lett. 1986, 48, 183-185.
(8) Brabec, C. J.; Sariciftci, N. S.; Hummelen, J. C. AdV. Funct. Mater. 2001, 11, 15-26.
(9) Kim, J. Y.; Lee, K.; Coates, N. E.; Moses, D.; Nguyen, T.-Q.; Dante, M.; Heeger, A. J. Science 2007, 317, 222-225.
(10) Aroca, R.; Del Cano, T.; de Saja, J. A. Chem. Mater. 2003, 15, 38-45.
(11) Snaith, H. J.; Whiting, G. L.; Sun, B. Q.; Greenham, N. C.; Huck, W. T. S.; Friend, R. H. Nano Lett. 2005, 9, 1653-1657.
(12) Kim, Y.; Cook, S.; Tuladhar, S. M.; Nelson, J.; Durrant, J. R.; Bradley, D. D. C.; Giles, M.; McCulloch, I.; Ha, C. S.; Ree, M. Nat. Mater. 2006, 5, 197-203.
(13) Yamamoto, Y.; Fukushima, T.; Saeki, A.; Seki, S.; Tagawa, S.; Ishii, N.; Aida, T. J. Am. Chem. Soc. 2007, 129, 9276-9277.
(14) Johkheijm, P.; Stutzmann, N.; Chen, Z. J.; de Leeuw, D. M.; Meijer, E. W.; Schenning, A. P. H. J.; Wurthner, F. J. Am. Chem. Soc. 2006, 128, 9535-9540.
(15) Garnier, F.; Yassar, A.; Hajlaoui, R.; Horowitz, G.; Deloffre, F.; Servet, B.; Ries, S.; Alnot, P. J. Am. Chem. Soc. 1993, 115, 8716-8721.
(16) Kastler, M.; Pisula, W.; Laquai, F.; Kumar, A.; Davies, R. J.; Baluschev, S.; Garcia-Gutierrez, M. C.; Wasserfullen, D.; Butt, H. J.; Riekel, C.; Wegner, G.; Mullen, K. AdV. Mater. 2006, 18, 2255-2259.
(17) Kline, R. J.; McGehee, M. D.; Toney, M. F. Nat. Mater. 2006, 5, 222-228.
(18) Duhm, S.; Heimel, G.; Salzmann, I.; Glowatzkl, H.; Johnson, R. L.; Vollmer, A.; Rabe, J. P.; Koch, N. Nat. Mater. 2008, 7, 326-332.
(19) Stoliar, P.; Kshirsagar, R.; Massi, M.; Annibale, P.; Albonetti, C.; de Leeuw, D. M.; Biscarini, F. J. Am. Chem. Soc. 2007, 129, 6477-6484.
(20) Holman, M. W.; Liu, R. C.; Adams, D. M. J. Am. Chem. Soc. 2003, 125, 12649-12654.
(21) Liu, M. S.; Niu, Y.-H.; Luo, J.; Chen, B.; Kim, T.-D.; Bardecker, J.; Jen, A. K.-Y. Polym. ReV. 2006, 46, 7-26.
(22) Hung, L. S.; Tang, C. W. Appl. Phys. Lett. 1999, 74, 3209-3211.
(23) Greenham, N. C.; Moratti, S. C.; Bradley, D. D. C.; Friend, R. H.; Holmes, A. B. Nature 1993, 365, 628-630.
(24) Brewer, P. J.; Lane, P. A.; deMello, A. J.; Bradley, D. D. C.; de Mello, J. C. AdV. Funct. Mater. 2004, 14, 562-570.
(25) Parker, I. D. J. Appl. Phys. 1994, 75, 1656-1666.
(26) Malliaras, G. G.; Scott, J. C. J. Appl. Phys. 1998, 83, 5399-5403.
(27) Ho, P. K. H.; Kim, J.-S.; Burroughes, J. H.; Becker, H.; Li, S. F. Y.; Brown, T. M.; Cacialli, F.; Friend, R. H. Nature 2000, 404, 481-484.
(28) Yang, X.; Müller, D. C.; Neher, D.; Meerholz, K. AdV. Mater. 2006, 18, 948-954.
(29) Hung, L. S.; Tang, C. W.; Mason, M. G. Appl. Phys. Lett. 1997, 70, 152-154.
(30) Li, F.; Tang, H.; Anderegg, J.; Shinar, J. Appl. Phys. Lett. 1997, 70, 1233-1235.
(31) Huang, J.; Li, G.; Wu, E.; Xu, Q.; Yang, Y. AdV. Mater. 2006, 18, 114-117.
(32) Ishii, H.; Sugiyama, K.; Ito, E.; Seki, K. AdV. Mater. 1999, 11, 605-625.
(33) Heimel, G.; Romaner, L.; Zojer, E.; Bredas, J.-L. Acc. Chem. Res. 2008, 4, 721-729.
(34) Shen, Y. L.; Hosseini, A. R.; Wong, M. H.; Malliaras, G. G. Chem. Phys. Chem. 2004, 5, 16-25.
(35) Campbell, I. H.; Joswick, M. D.; Parker, I. D. Appl. Phys. Lett. 1995, 67, 3171-3173.
(36) Hoven, C. V.; Peet, J.; Mikhailovsky, A.; Nguyen, T.-Q. Appl. Phys. Lett. 2009, 94, 033301. 1-3.
(37) Huang, F.; Wu, H. B.; Wang, D.; Yang, W.; Cao, Y. Chem. Mater. 2004, 16, 708-716.
(38) Hoven, C. V.; Garcia, A.; Bazan, G. C.; Nguyen, T. Q. AdV. Mater. 2008, 20, 3793-3810.

(39) Yang, R. Q.; Wu, H. B.; Cao, Y.; Bazan, G. C. J. Am. Chem. Soc. 2006, 128, 14422-14423.
(40) Steuerman, D. W.; Garcia, A.; Dante, M.; Yang, R.; Lofvander, J. P.; Nguyen, T. Q. AdV. Mater. 2008, 20, 528-534.
(41) Hoven, C.; Yang, R.; Garcia, A.; Heeger, A. J.; Nguyen, T. Q.; Bazan, G. C. J. Am. Chem. Soc. 2007, 129, 10976-10977.
(42) Hoven, C. V.; Yang, R.; Garcia, A.; Crockett, V.; Heeger, A. J.; Bazan, G. C.; Nguyen, T. Q. Proc. Natl. Acad. Sci. U.S.A. 2008, 105, 12730-12735.
(43) Yang, R. Q.; Xu, Y. H.; Dang, X. D.; Nguyen, T. Q.; Cao, Y.; Bazan, G. C. J. Am. Chem. Soc. 2008, 130, 3282-3283.
(44) Xu, Y. H.; Yang, R. Q.; Peng, J. B.; Mikhailovsky, A. A.; Cao, Y.; Nguyen, T.-Q.; Bazan, G. C. AdV. Mater. 2009, 21, 584-588.
(45) Ziegler, C. J. US Patent 20060124902A1.
(46) Hamilton, B. H.; Kelly, K. A.; Malasi, W.; Ziegler, C. J. Inorg. Chem. 2003, 42, 3067-3073.
(47) Kirchmeyer, S.; Reuter, K. J. Mater. Chem. 2005, 15, 2077-2088.
(48) Tang, H.; Li, F.; Shinar, J. Appl. Phys. Lett. 1997, 71, 2560-2562.
(49) Hsiao, C.-C.; Hsiao, A.-E.; Chen, S.-A. AdV. Mater. 2008, 20, 1982-1988.
(50) Tang, C. W.; Vanslyke, S. A.; Chen, C. H. J. Appl. Phys. 1989, 65, 3610-3616.
(51) Cao, Y.; Yu, G.; Heeger, A. J. AdV. Mater. 1999, 10, 917-920.
(52) Huang, F.; Hou, L. T.; Wu, H. B.; Wang, X. H.; Shen, H. L.; Cao, W.; Yang, W.; Cao, Y. J. Am. Chem. Soc. 2004, 126, 9845-9853.
(53) Wu, H.; Huang, F.; Mo, Y.; Yang, W.; Wang, D.; Peng, J.; Cao, Y. AdV. Mater. 2004, 16, 1826-1830.
(54) Pei, Q. B.; Zhang, C.; Yang, Y.; Heeger, A. J. Science 1995, 269, 1086-1088.
(55) Pei, Q. B.; Yang, Y.; Yu, G.; Zhang, C.; Heeger, A. J. J. Am. Chem. Soc. 1996, 118, 3922-3929.
(56) Stinker, J. D.; DeFranco, J. A.; Jaqith, M. J.; Silveira, R.; Zhong, Y.-W.; Moran-Mirabal, J. M.; Craighead, H. G.; Abruña, H. D.; Marohn, J. A.; Malliaras, G. G. Nat. Mater. 2007, 6, 894-899.
(57) Pingree, L. S. C.; Rodovsky, D. B.; Coffey, D. C.; Bartholomew, G. P.; Ginger, D. S. J. Am. Chem. Soc. 2007, 129, 15903-15910.
(58) Coffey, D. C.; Ginger, D. S. Nat. Mater. 2006, 5, 735-740.
(59) Hoppe, H.; Glatzel, T.; Niggemann, M.; Hinsch, A.; Lux-Steiner, M. C.; Sariciftci, N. S. Nano Lett. 2005, 5, 269-274.
(60) Chiesa, M.; Burgi, L.; Kim, J. S.; Shikler, R.; Friend, R. H.; Sirringhaus, H. Nano Lett. 2005, 5, 559-563.
(61) Liscio, A.; De Luca, G.; Nolde, F.; Palermo, V.; Mullen, K.; Samori, P. J. Am. Chem. Soc. 2008, 130, 780-781.
(62) Girard, P. Nanotechnology 2001, 12, 485-490.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A polymer light-emitting diode (PLED) device comprising an emissive layer and an electron injection layer comprising a zwitterionic material selected from one of the following:

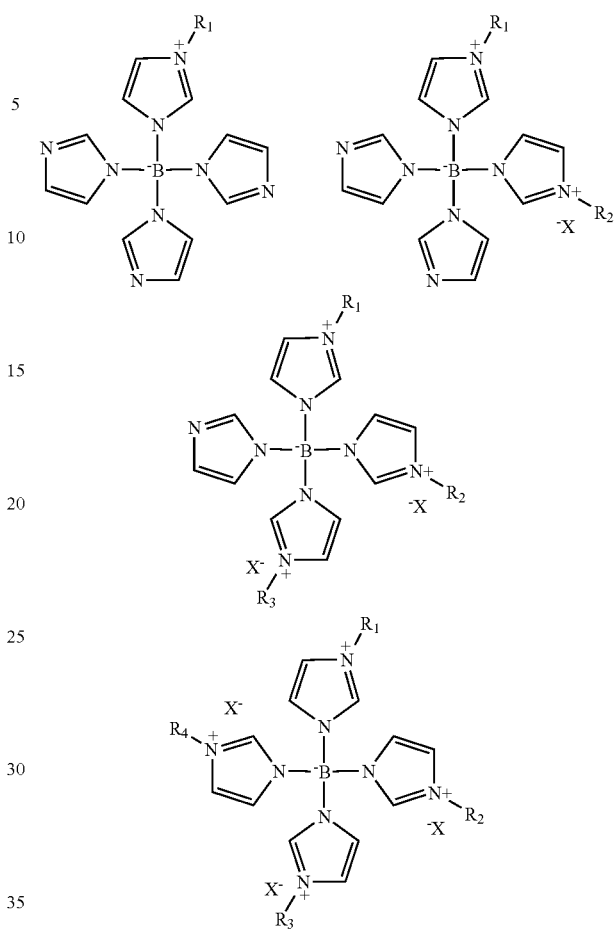

wherein $R_1$, $R_2$, $R_3$ and $R_4$ are each independently selected from an alkyl group of the formula $C_nH_{2n+1}$, wherein n is an integer from 1-20 and wherein $X^-$ is a charge compensating anion.

2. A zwitterionic material comprising: a compound selected from one of the following:

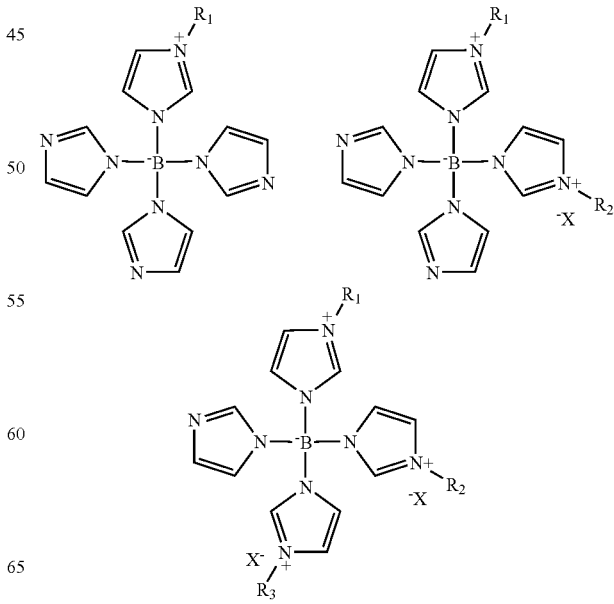

-continued

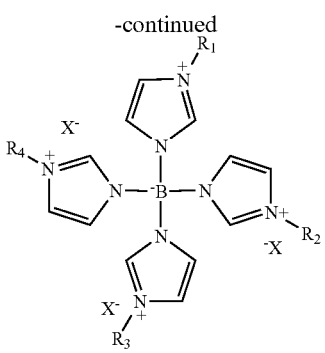

wherein $R_1$, $R_2$, $R_3$ and $R_4$ are each independently selected from the group consisting of $C_6H_{13}$, $C_{10}H_{21}$, $C_{12}H_{25}$ and $C_{16}H_{33}$ and wherein $X^-$ is a charge compensating anion.

3. The device of claim 1, wherein $R_1$, $R_2$, $R_3$ and $R_4$ are each independently selected from the group consisting of a $CH_3$, $C_6H_{13}$, $C_{10}H_{21}$, $C_{12}H_{25}$ and $C_{16}H_{33}$ group.

4. The device of claim 1, wherein the material is incorporated into a PLED device using a solution process method.

* * * * *